US006992080B2

(12) United States Patent
Dwyer et al.

(10) Patent No.: US 6,992,080 B2
(45) Date of Patent: Jan. 31, 2006

(54) IMIDAZOPYRIDINES AS CYCLIN DEPENDENT KINASE INHIBITORS

(75) Inventors: Michael P. Dwyer, Scotch Plains, NJ (US); Timothy J. Guzi, Chatham, NJ (US); Kamil Paruch, Garwood, NJ (US); Ronald J. Doll, Convent Station, NJ (US); Kartik M. Keertikar, East Windsor, NJ (US); Viyyoor M. Girijavallabhan, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/664,338

(22) Filed: Sep. 17, 2003

(65) Prior Publication Data

US 2004/0097517 A1    May 20, 2004

Related U.S. Application Data

(60) Provisional application No. 60/412,063, filed on Sep. 19, 2002.

(51) Int. Cl.
*A61K 31/435* (2006.01)
*A61K 31/505* (2006.01)
*A61K 31/44* (2006.01)
*C07D 471/02* (2006.01)
*C07D 401/14* (2006.01)

(52) U.S. Cl. ............... 514/217.07; 514/303; 514/300; 514/253.04; 514/256; 544/362; 544/333; 546/121; 546/113

(58) Field of Classification Search ............... 546/121, 546/113; 544/333, 362; 540/597; 514/300, 514/303, 256, 253.04, 217.07
See application file for complete search history.

(56) References Cited

U.S. PATENT DOCUMENTS 5,574,042 A * 11/1996 Oku et al. ................. 514/300
2004/0018192 A1   1/2004 Wakabayashi et al.

FOREIGN PATENT DOCUMENTS

| EP | 0 673 937 | 9/1995 |
|---|---|---|
| WO | WO 96/34866 | 11/1996 |
| WO | WO 98/37080 | 8/1998 |
| WO | WO 99/55706 | 11/1999 |
| WO | WO 01/56607 | 8/2001 |
| WO | WO 02/20523 | 3/2002 |

OTHER PUBLICATIONS

Diego Basso et al., "Synthetic Approach to Imidazo[1,2-α] pyridine Derivatives by the Intramolecular Nitrone Cycloaddition Methodology", *Tetrahedron*, 58, 4445-4450 (2002).
E. Smakula Hand et al., "Teleamination of the Imidazo[1,2-a]pyridine System", *J. Org. Chem.*, 43(14), 2900-2906 (1978).
Vesely et al., "Inhibition of Cyclin-Dependent Kinases by Purine Analogues", *Eur. J. Biochem.* (1994), 224: 771-786.
Senderowicz et al., "Phase I Trial of Continuous Infusion Flavopiridol, a Novel Cyclin-Dependent Kinase Inhibitor, in Patients with Refractory Neoplasams", *Journal of Clinical Oncology* (Sep. 1998), 16(9): 2986-2999.
Meijer et al., "Biochemical and Cellular Effects of Roscovitine, a Potent and Selective Inhibitor of the Cyclin-Dependent Kinases CDC2, CDK2 and CDK5", *Eur. J. Biochem.* (1997), 243: 527-536.
Bible et al., "Cytotoxic Synergy between Flavopiridol (NSC 649890, L86-8275) and Various Antineoplastic Agents: The Importance of Sequence of Administration", *Cancer Research* (Aug. 15, 1997), 57: 3375-3380.
Shiota et al., "Synthesis and Structure-Activity Relationship of a New Series of Potent Angiotensin II Receptor Antagonists: Pyrazolo[1,5-α]pyrimidine", *Chem. Pharm. Bull.* (1999), 47(7): 928-938.
Yasuo Makisumi, "Studies on the Azaindolizine Compounds. XI. Synthesis of 6,7-Disubstituted Pyrazolo[1,5-α]pyrimidines.", *Chem. Pharm. Bull.* (1962), 10: 620-626.

* cited by examiner

*Primary Examiner*—Cecilia Tsang
*Assistant Examiner*—Lexington A. Hoffman
(74) *Attorney, Agent, or Firm*—Palaiyur S. Kalyanaraman

(57) ABSTRACT

In its many embodiments, the present invention provides a novel class of imidazo[1,2-a]pyridine compounds as inhibitors of cyclin dependent kinases, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the CDKs using such compounds or pharmaceutical compositions.

16 Claims, No Drawings

IMIDAZOPYRIDINES AS CYCLIN DEPENDENT KINASE INHIBITORS

This application claims the benefit of priority from U.S. provisional patent application Ser. No. 60/412,063, filed Sep. 19, 2002.

FIELD OF THE INVENTION

The present invention relates to imidazo[1,2-a]pyridine compounds useful as protein kinase inhibitors (such as for example, the inhibitors of the cyclin-dependent kinases, mitogen-activated protein kinase (MAPK/ERK), glycogen synthase kinase 3(GSK3beta) and the like), pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases.

BACKGROUND OF THE INVENTION

Protein kinase inhibitors include kinases such as, for example, the inhibitors of the cyclin-dependent kinases (CDKs), mitogen activated protein kinase (MAPK/ERK), glycogen synthase kinase 3 (GSK3beta), and the like. The cyclin-dependent kinases are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al., J. Clin. Oncol. (1998) 16, 2986–2999.

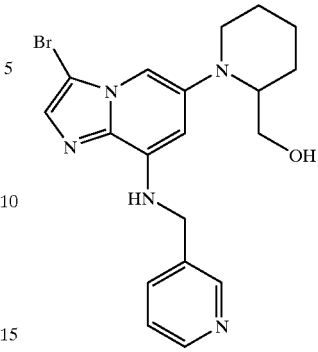

Other known inhibitors of the CDKs include, for example, olomoucine (J. Vesely et al, Eur. J. Biochem., (1994) 224, 771–786) and roscovitine (I. Meijer et al, Eur. J. Biochem., (1997) 243, 527–536). U.S. Pat. No. 6,107,305 describes certain pyrazolo[3,4-b]pyridine compounds as CDK inhibitors. An illustrative compound from the '305 patent has the Formula II:

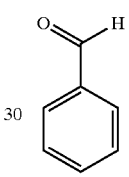

K. S. Kim et al, J. Med. Chem. 45 (2002) 3905–3927 and WO 02/10162 disclose certain aminothiazole compounds as CDK inhibitors.

Pyrazolopyrimidines are known. For Example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383,790, Chem. Pharm. Bull., (1999) 47 928, J. Med. Chem., (1977) 20, 296, J. Med. Chem., (1976) 19 517 and Chem. Pharm. Bull., (1962) 10 620 disclose various pyrazolopyrimidines.

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, the present invention provides a novel class of imidazo[1,2-a]pyridine compounds as inhibitors of cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the CDKs using such compounds or pharmaceutical compositions.

In one aspect, the present application discloses a compound, or pharmaceutically acceptable salts or solvates of said compound, said compound having the general structure shown in Formula III:

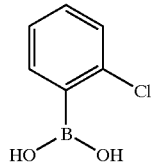

wherein:

R is selected from the group consisting of alkyl, aryl, heteroaryl, heteroarylalkyl, heterocyclyl, heterocyclylalkyl, arylalkyl, cycloalkyl, —NR⁶R⁷, —C(O)R⁷, —C(O)OR⁶, —C(O)NR⁶R⁷ and —S(O₂)R⁷, wherein each of said alkyl, aryl, heteroaryl, heteroarylalkyl, heterocyclyl, heterocyclylalkyl, cycloalkyl and arylalkyl can be unsubstituted or optionally independently substituted with one or more moieties which can be the same or different, each moiety being independently selected from the group consisting of halogen, alkyl, cycloalkyl, CF₃, CN, —OCF₃, —OR⁶, —C(O)R⁷, —NR⁶R⁷, —C(O)OR⁶, —C(O)NR⁵R⁶, —SR⁶, —S(O₂)R⁷, —S(O₂)NR⁵R⁶, —N(R⁵)S(O₂)R⁷, —N(R⁵)C(O)R⁷ and —N(R⁵)C(O)NR⁵R⁶ and NO₂;

R² is selected from the group consisting of H, R⁹, alkyl, aryl, arylalkyl, heteroaryl, heteroarylalkyl, heterocyclyl, heterocyclylalkyl, alkenyl, alkynyl, cycloalkyl, —CF₃, —C(O)R⁷, alkyl substituted with 1–6 R⁹ groups which groups can be the same or different with each R⁹ being independently selected,

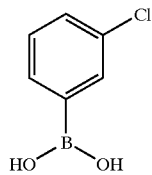

wherein each of said aryl, heteroaryl, arylalkyl and heterocyclyl can be unsubstituted or optionally independently substituted with one or more moieties which can be the same or different, each moiety being independently selected from the group consisting of halogen, alkyl, cycloalkyl, CF₃, CN, —OCF₃, —OR⁶, —C(O)R⁷, —NR⁶R⁷, —C(O)OR⁶, —C(O)NR⁵R⁶, —SR⁶, —S(O₂)R⁷, —S(O₂)NR⁵R⁶, —N(R⁵)S(O₂)R⁷, —N(R⁵)C(O)R⁷ and —N(R⁵)C(O)NR⁵R⁶;

R³ is selected from the group consisting of H, halogen, —NR⁵R⁶, CF₃, alkyl, cycloalkyl, aryl, heteroaryl, heteroarylalkyl, heterocyclyl, heterocyclylalkyl, alkynyl, alkenyl, —(CHR⁵)ₙ-aryl, —(CHR⁵)ₙ-heteroaryl, —(CHR⁵)ₙ—OR⁶, —S(O₂)R⁶, —C(O)R⁶, —S(O₂)NR⁵R⁶, —C(O)OR⁶, —C(O)NR⁵R⁶, —CH(aryl)₂, —(CH₂)ₘ—NR⁸,

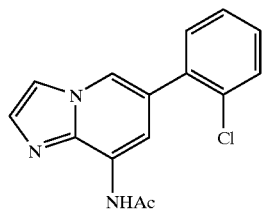

wherein each of said aryl, alkyl, arylalkyl, cycloalkyl, heteroaryl, heteroarylalkyl, heterocyclyl and heterocyclylalkyl for R³ and the heterocyclyl moieties whose structures are shown immediately above for R³ can be unsubstituted or optionally independently substituted with one or more moieties which moieties can be the same or different, each moiety being independently selected from the group consisting of halogen, alkyl, aryl, cycloalkyl, CF₃, CN, —OCF₃, —OR⁵, —C(R⁴R⁵)ₙOR⁵, —NR⁵R⁶, —C(R⁴R⁵)ₙNR⁵R⁶, —C(O₂)R⁵, —C(O)R⁵, —C(O)NR⁵R⁶, —SR⁶, —S(O₂)R⁶, —S(O₂)NR⁵R⁶, —N(R⁵)S(O₂)R⁷, —N(R⁵)C(O)R⁷ and —N(R⁵)C(O)NR⁵R⁶;

R⁴ is selected from the group consisting of H, halogen, CF₃, alkyl, cycloalkyl, aryl, heteroaryl, heteroarylalkyl, heterocyclyl, heterocyclylalkyl, alkynyl, alkenyl, —(CHR⁵)ₙ-aryl, —(CHR⁵)ₙ-heteroaryl, —(CHR⁵)ₙ—OR⁶, —S(O₂)R⁶, —C(O)R⁶, —S(O₂)NR⁵R⁶, —C(O)OR⁶, —C(O)NR⁵R⁶, cycloalkyl, —CH(aryl)₂, —(CH₂)ₘ—NR⁸, and

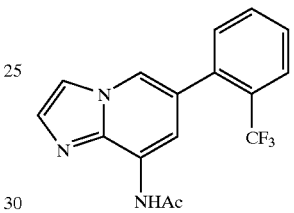

wherein each of said aryl, alkyl, cycloalkyl, heteroaryl, heteroarylalkyl, heterocyclyl and heterocyclylalkyl can be unsubstituted or optionally substituted with one or more moieties which can be the same or different, each moiety being independently selected from the group consisting of halogen, alkyl, aryl, cycloalkyl, CF₃, CN, —OCF₃, —OR⁵, —NR⁵R⁶, —C(O₂)R⁵, —C(O)NR⁵R⁶, —SR⁶ and —S(O₂)R⁶;

R⁵ is H, alkyl or aryl;

R⁶ is selected from the group consisting of H, alkyl, aryl, heteroaryl, arylalkyl, cycloalkyl, heteroarylalkyl, heterocyclyl and heterocyclylalkyl, wherein each of said alkyl, aryl, heteroaryl, arylalkyl, cycloalkyl, heteroarylalkyl, heterocyclyl and heterocyclylalkyl can be unsubstituted or optionally independently substituted with one or more moieties which can be the same or different, each moiety being independently selected from the group consisting of halogen, alkyl, aryl, cycloalkyl, heterocyclylalkyl, CF₃, OCF₃, CN, —OR⁵, —NR⁵R¹⁰, —N(R⁵)Boc, —C(R⁴R⁵)OR⁵, —C(O)R⁶, —C(O)OR⁵, —C(O)NR⁵R¹⁰, —SO₃H, —SR¹⁰, —S(O₂)R⁷, —S(O₂)NR⁵R¹⁰, —N(R⁵)S(O₂)R⁷, —N(R⁵)C(O)R⁷ and —N(R⁵)C(O)NR⁵R¹⁰;

R¹⁰ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, CF₃, OCF₃, CN, —OR⁵, —NR⁴R⁵, —N(R⁵)Boc, —(CR⁴R⁵)ₙOR⁵, —C(O₂)R⁵, —C(O)

$NR^4R^5$, —$C(O)R^5$, —$SO_3H$, —$SR^5$, —$S(O_2)R^7$, —$S(O_2)NR^4R^5$, —$N(R^5)S(O_2)R^7$, —$N(R^5)C(O)R^7$ and —$N(R^5)C(O)NR^4R^5$;

or optionally (i) $R^5$ and $R^{10}$ in the moiety —$NR^5R^{10}$, or (ii) $R^5$ and $R^6$ in the moiety —$NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, heteroaryl, arylalkyl and heteroarylalkyl wherein each of said alkyl, cycloalkyl, heteroarylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$CH_2OR^5$, —$C(O_2)R^5$, —$C(O)NR^5R^{10}$, —$C(O)R^5$, —$SR^{10}$, —$S(O_2)R^{10}$, —$S(O_2)NR^5R^{10}$, —$N(R^5)S(O_2)R^{10}$, —$N(R^5)C(O)R^{10}$ and —$N(R^5)C(O)NR^5R^{10}$;

$R^8$ is selected from the group consisting of $R^6$, —$C(O)NR^5R^{10}$, —$S(O_2)NR^5R^{10}$, —$C(O)R^7$, —$C(O)OR^6$ and —$S(O_2)R^7$;

$R^9$ is selected from the group consisting of halogen, CN, $NR^5R^{10}$, —$C(O)OR^6$, —$C(O)NR^5R^{10}$, —$OR^6$, —$C(O)R^7$, —$SR^6$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{11}$ is H, alkyl or aryl;

m is 0 to 4; and n is 1–4.

The compounds of Formula III can be useful as protein kinase inhibitors and can be useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION

In one embodiment, the present invention discloses imidazo[1,2-a]pyridine compounds which are represented by structural Formula III, or a pharmaceutically acceptable salt or solvate thereof, wherein the various moieties are as described above.

In another embodiment, R is selected from the group consisting of aryl, arylalkyl, heteroaryl, heteroarylalkyl, alkyl, —$S(O_2)R^7$, and —$C(O)R^7$, wherein each of said aryl, arylalkyl, heteroaryl, heteroarylalkyl and alkyl can be unsubstituted or optionally independently substituted with one or more moieties which can be the same or different, each moiety being independently selected from the group consisting of halogen, alkyl, $CF_3$, CN, —$OCF_3$, —$NR^6R^7$, —$N(R^5)C(O)R^7$, and —$OR^6$.

In another embodiment, $R^2$ is selected from the group consisting of halogen, alkyl, aryl, heteroaryl, alkenyl and —$C(O)R^7$, wherein each of said alkyl, aryl and heteroaryl can be unsubstituted or optionally independently substituted with one or more moieties which can be the same or different, each moiety being independently selected from the group consisting of halogen, alkyl, $CF_3$, CN, —$OCF_3$, and —$OR^6$.

In another embodiment, $R^3$ is selected from the group consisting of H, aryl, heteroaryl, —$(CHR^5)_n$-aryl, —$(CHR^5)_n$-heteroaryl, —$(CHR^5)_n$—$OR^6$, —$C(O)R^6$, cycloalkyl, —$NR^5R^6$, —$CH(aryl)_2$,

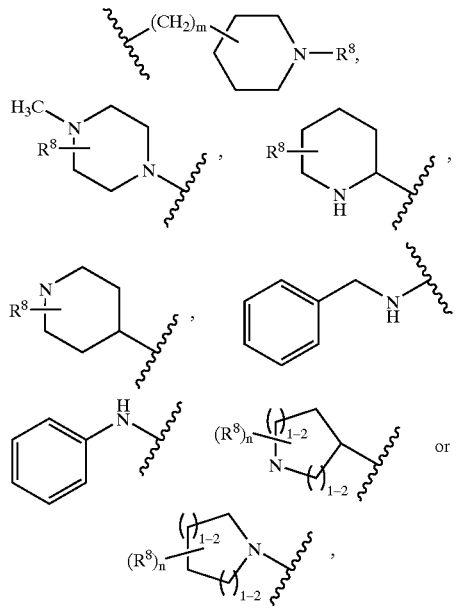

wherein each of said aryl, cycloalkyl and heteroaryl and the heterocyclyl structures shown immediately above for $R^3$ can be substituted or optionally independently substituted with one or more moieties which can be the same or different, each moiety being independently selected from the group consisting of halogen, $CF_3$, $OCF_3$, alkyl, CN, aryl, —$C(O)R^5$, —$C(O_2)R^5$, —$S(O_2)R^6$, —$C(=NH)$—$NH_2$, —$C(=CN)$—$NH_2$, hydroxyalkyl, alkoxycarbonyl, —$SR^6$, and $OR^5$, with the proviso that no carbon adjacent to a nitrogen atom on a heterocyclyl ring carries a —$OR^5$ moiety.

In another embodiment of a compound of Formula III, $R^4$ is selected from the group consisting of H, alkyl, aryl, heteroaryl, —$(CHR^5)_n$-aryl, —$(CHR^5)_n$-heteroaryl, —$(CHR^5)_n$, —$OR^6$, —$C(O)R^6$, cycloalkyl, —$CH(aryl)_2$ and

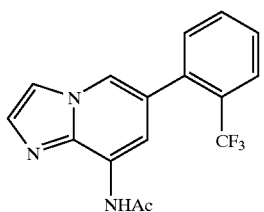

wherein each of said aryl and heteroaryl can be unsubstituted or optionally substituted with one or more moieties which can be the same or different, each moiety being independently selected from the group consisting of halogen, alkyl, aryl, $CF_3$, CN, —$C(O_2)R^5$ and —$S(O_2)R^6$.

In another embodiment, $R^5$ is H, aryl or lower alkyl.

In another embodiment of a compound of Formula III, $R^{11}$ is H or lower alkyl.

In another embodiment, m is 0 to 2.

In another embodiment, n is 1 to 3.

In an additional embodiment, R is selected from the group consisting of phenyl, benzyl, benzoyl, phenylsulfonyl, thienyl, thienylalkyl, thienylcarbonyl, thienylsulfonyl, furyl, furylalkyl, furylcarbonyl, furylsulfonyl, pyridyl, pyridylalkyl, pyridylcarbonyl, pyridylsulfonyl, pyrrolyl, pyrrolylalkyl, pyrrolylcarbonyl, pyrrolylsulfonyl, oxazolyl, oxazolylalkyl, oxazolylcarbonyl, oxazolylsulfonyl, thiazolyl, thiazolylalkyl, thiazolylcarbonyl, thiazolylsulfonyl, pyrazinyl, pyrazinylalkyl, pyrazinylcarbonyl, pyrazinylsulfonyl, pyridazinyl, pyridazinylalkyl, pyridazinylcarbonyl, pyridazinylsulfonyl, pyrimidinyl, pyrimidinylalkyl, pyrimidinylcarbonyl, pyrimidinylsulfonyl, —S(O$_2$)CH$_3$, and —C(O)CH$_3$, as well as their applicable N-oxides, wherein each of said phenyl (including the phenyl of the benzyl), thienyl, furyl, pyridyl, pyrrolyl, oxazolyl, thiazolyl, pyrazinyl, pyridazinyl and pyrimidinyl can be unsubstituted or optionally independently substituted with one or more moieties which can be the same or different, each moiety being independently selected from the group consisting of Cl, Br, I, lower alkyl, CF$_3$, CN, —C(O)OR$^6$, —NR$^6$R$^7$, —N(R$^5$)C(O)R$^7$, —OCF$_3$, and —OH.

In an additional embodiment, R is unsubstituted phenyl, unsubstituted pyridyl, benzyl whose phenyl can be unsubstituted or optionally substituted with one or more moieties selected from the group consisting of F, Cl, Br, CN, CF$_3$, —NH$_2$, and —N(H)C(O)CH$_3$, benzoyl whose phenyl can be unsubstituted or optionally substituted with one or more moieties selected from the group consisting of F, Cl, Br, CN, CF$_3$, —NH$_2$, and —N(H)C(O)CH$_3$, phenylsulfonyl whose phenyl can be unsubstituted or optionally substituted with one or more moieties selected from the group consisting of F, Cl, Br, CN, —NH$_2$, —N(H)C(O)CH$_3$ and CF$_3$, pyridylmethyl whose pyridyl can be unsubstituted or optionally substituted with one or more moieties selected from the group consisting of F, Cl, Br, CN, CF$_3$, —NH$_2$, and —N(H)C(O)CH$_3$, pyridylcarbonyl whose pyridyl can be unsubstituted or optionally substituted with one or more moieties selected from the group consisting of F, Cl, Br, CN, CF$_3$, —NH$_2$, and —N(H)C(O)CH$_3$, pyridylsulfonyl whose pyridyl can be unsubstituted or optionally substituted with one or more moieties selected from the group consisting of F, Cl, Br, CN, —NH$_2$, —N(H)C(O)CH$_3$ and CF$_3$, pyrimidylmethyl whose pyrimidylmethyl can be unsubstituted or optionally substituted with one or more moieties selected from the group consisting of F, Cl, Br, CN, —NH$_2$, —N(H)C(O)CH$_3$ and CF$_3$, pyrimidylcarbonyl whose pyrimidyl can be unsubstituted or optionally substituted with one or more moieties selected from the group consisting of F, Cl, Br, CN, —NH$_2$, —N(H)C(O)CH$_3$ and CF$_3$, or pyrimidylsulfonyl whose pyrimidyl can be unsubstituted or optionally substituted with one or more moieties selected from the group consisting of F, Cl, Br, CN, —NH$_2$, —N(H)C(O)CH$_3$ and CF$_3$.

In an additional embodiment, R$^2$ is H, F, Cl, Br, I, hydroxyalkyl, alkoxyalkyl, or lower alkyl.

In an additional embodiment, R$^3$ is H, alkyl, aryl, —NR$^5$R$^6$,

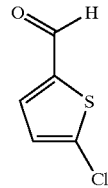

wherein said alkyl and aryl and the heterocyclyl moieties shown immediately above for R$^3$ can be unsubstituted or optionally independently substituted with one or more moieties (in addition to any R$^8$) which can be the same or different, each moiety being independently selected from the group consisting of F, Cl, Br, CF$_3$, lower alkyl, hydroxyalkyl, alkoxy, —S(O$_2$)R$^6$, and CN.

In an additional embodiment, R$^4$ is H, alkyl or aryl, wherein said alkyl or aryl can be unsubstituted or optionally independently substituted with one or more moieties which can be the same or different, each moiety being independently selected from the group consisting of F, Cl, Br, CF$_3$, lower alkyl, hydroxyalkyl, alkoxy, —S(O$_2$)R$^6$, and CN.

In an additional embodiment, R$^5$ is H.

In an additional embodiment, R$^{11}$ is H.

In an additional embodiment, m is 0.

In an additional embodiment, n is 1 or 2.

An inventive group of compounds is shown in Table 1.

TABLE 1

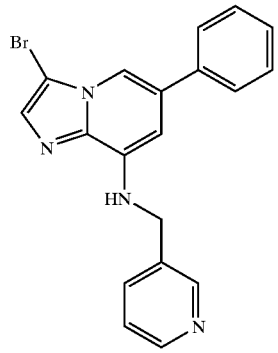

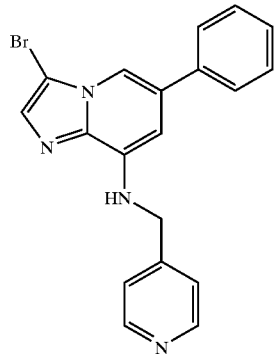

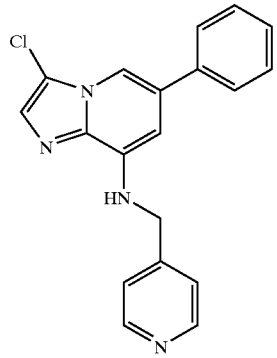

TABLE 1-continued
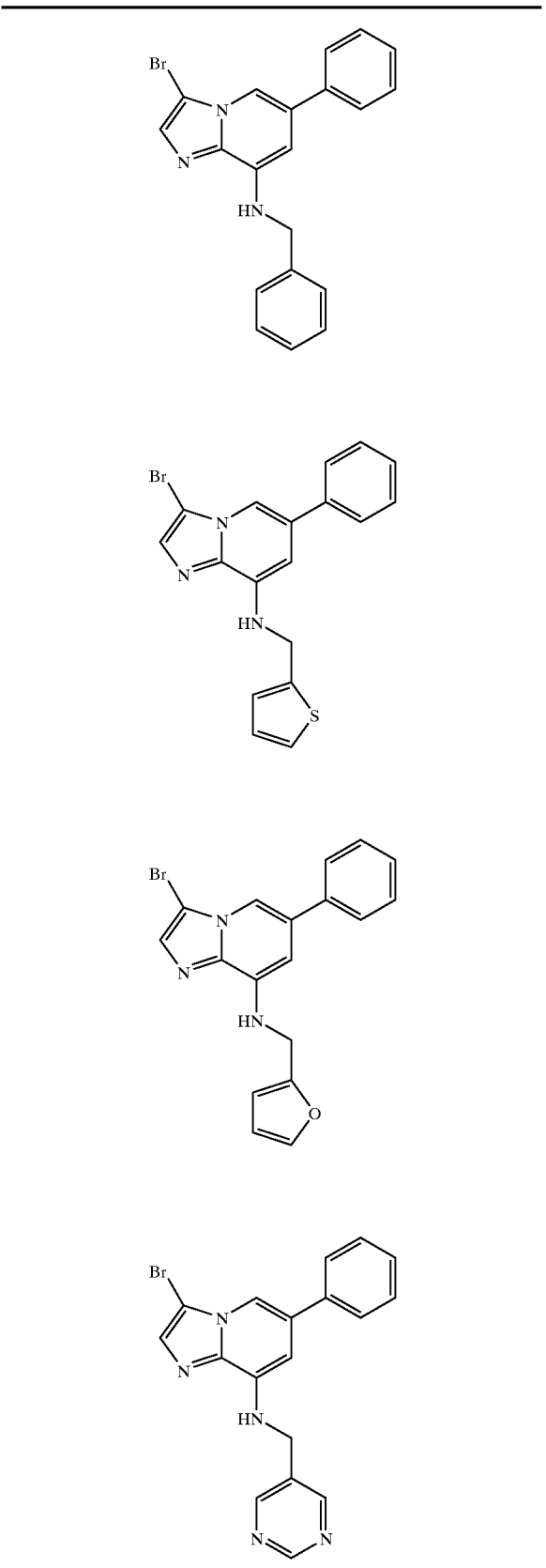
TABLE 1-continued
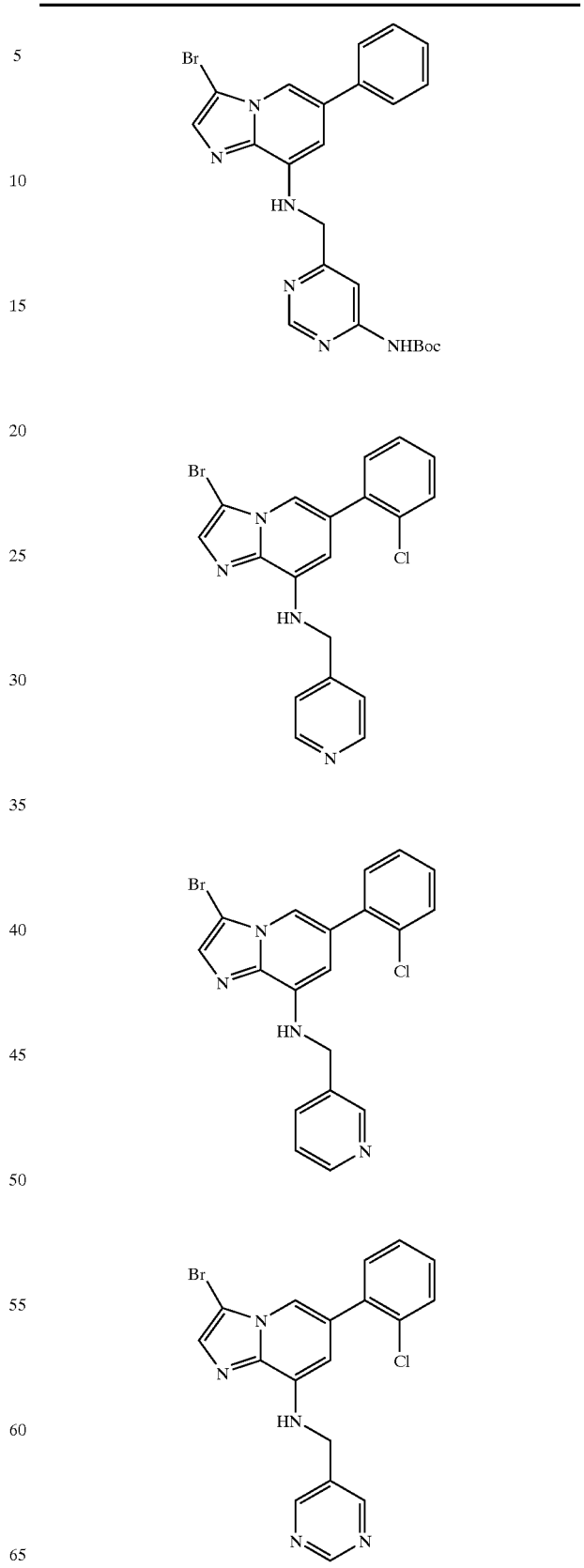

TABLE 1-continued
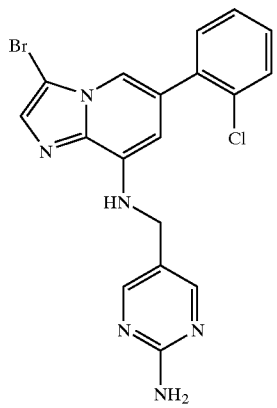
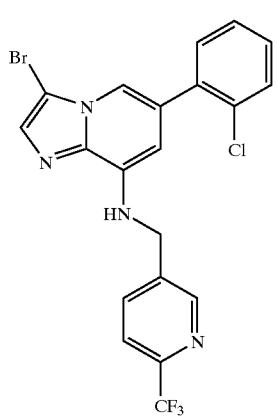
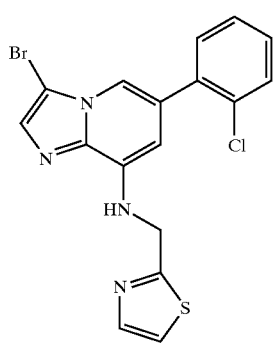
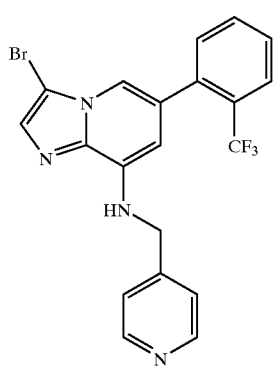
TABLE 1-continued
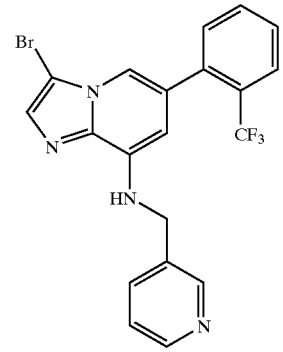
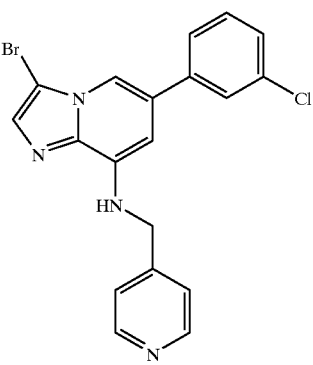
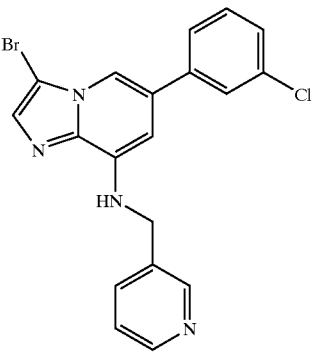
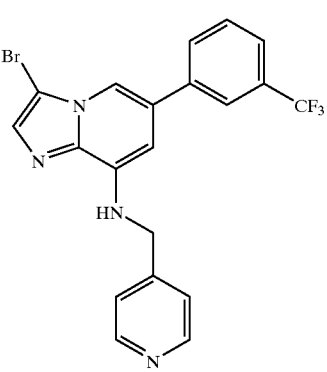

TABLE 1-continued
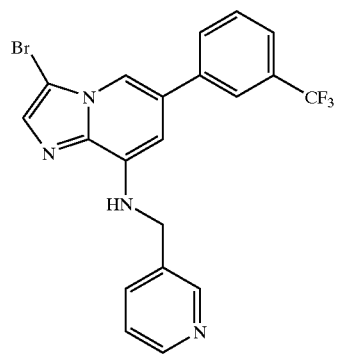
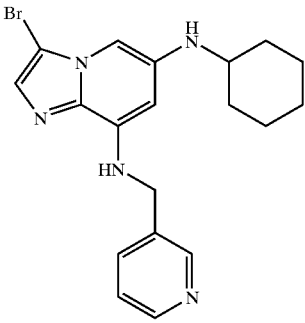
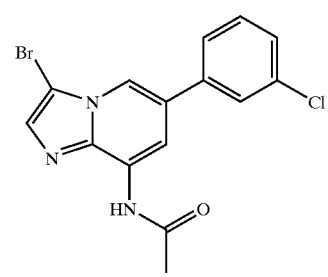
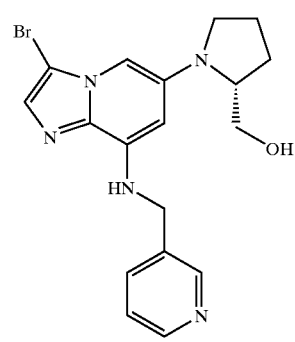
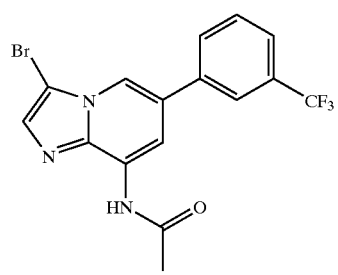
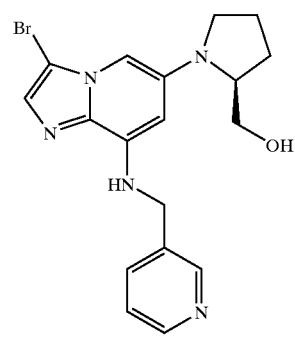
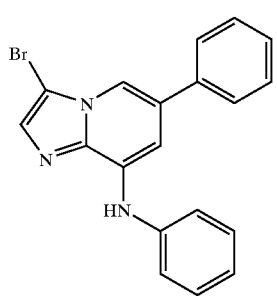
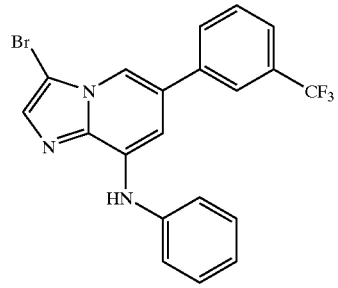
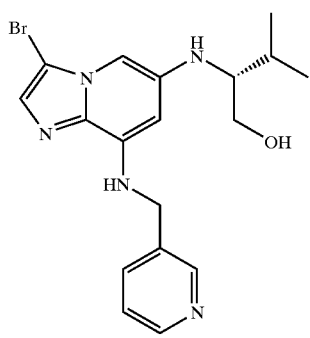

TABLE 1-continued

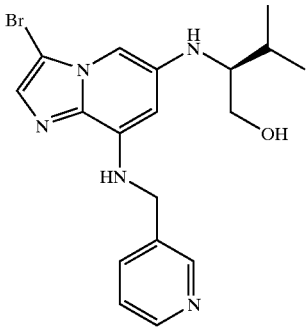

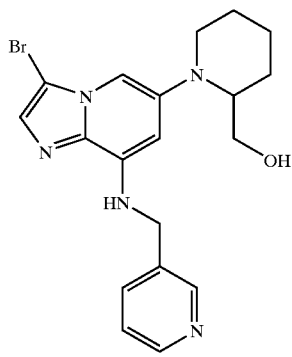

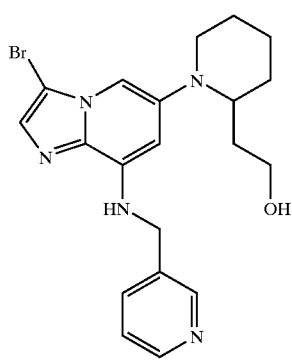

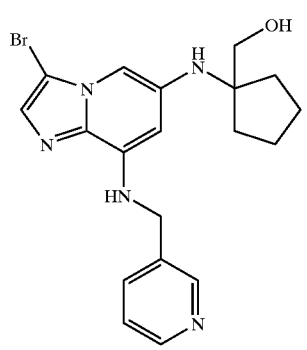

TABLE 1-continued

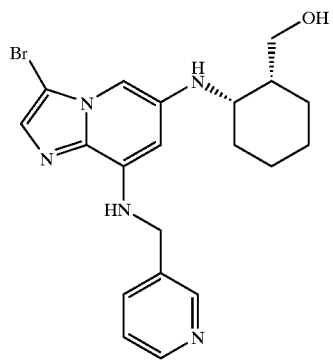

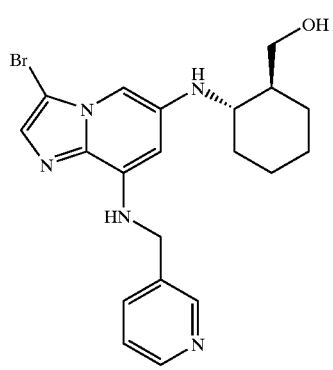

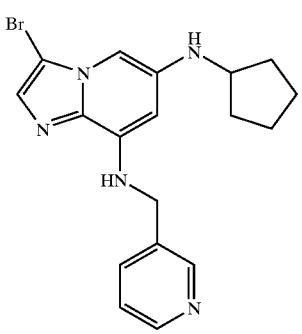

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

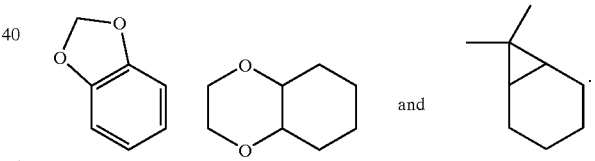

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

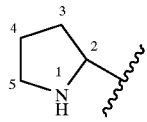

there is no —OH attached directly to carbons marked 2 and 5.

It should also be noted that tautomeric forms such as, for example, the moieties:

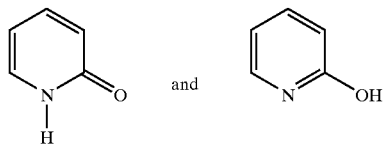

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula III, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula III or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula III can form salts which are also within the scope of this invention. Reference to a compound of Formula III herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula III may be formed, for example, by reacting a compound of Formula III respectively with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula III, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The compounds according to the invention have pharmacological properties; in particular, the compounds of Formula III can be inhibitors of protein kinases such as, for example, the inhibitors of the cyclin-dependent kinases, mitogen-activated protein kinase (MAPK/ERK), glycogen synthase kinase 3(GSK3beta) and the like. The cyclin dependent kinases (CDKs) include, for example, CDC2 (CDK1), CDK2, CDK4, CDK5, CDK6, CDK7 and CDK8. The novel compounds of Formula III are expected to be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of Formula III can be useful in the treatment of a variety of cancers, including (but not limited to) the following: carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula III may also be useful in the treatment of Alzheimer's disease, as suggested by the recent finding that CDK5 is involved in the phosphorylation of tau protein (J. Biochem, (1995) 117, 741–749).

Compounds of Formula III may induce or inhibit apoptosis. The apoptotic response is aberrant in a variety of human diseases. Compounds of Formula III, as modulators of apoptosis, will be useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula III, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula III may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula III may also be useful in inhibiting tumor angiogenesis and metastasis.

Compounds of Formula III may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of Formula III, or a pharmaceutically acceptable salt or solvate of said compound to the mammal.

A preferred dosage is about 0.001 to 500 mg/kg of body weight/day of the compound of Formula III. An especially preferred dosage is about 0.01 to 25 mg/kg of body weight/day of a compound of Formula III, or a pharmaceutically acceptable salt or solvate of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™(4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formula III may also be administered sequentially with known anticancer or cytotoxic agents when a combination formulation is inappropriate. The invention is not limited in the sequence of administration; compounds of Formula III may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of Formula III, or a pharmaceutically acceptable salt or solvate thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula III, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula III, or a pharmaceutically acceptable salt or solvate of said compound and a pharmaceutically acceptable carrier, vehicle or diluent.

Yet another aspect of this invention is a kit comprising an amount of at least one compound of Formula III, or a pharmaceutically acceptable salt or solvate of said compound and an amount of at least one anticancer therapy and/or anti-cancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:

Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: µl
grams: g
milligrams: mg
room temperature or rt (ambient): about 25° C.

EXAMPLES

Scheme 1

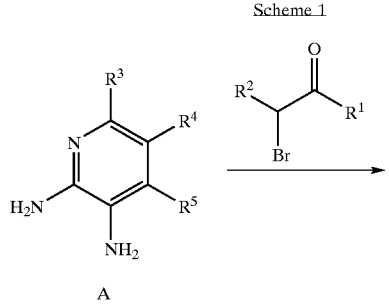

A

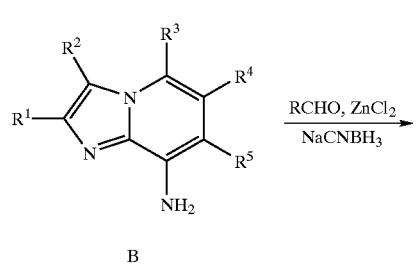

B

For the preparation of compounds (R$^2$=H; R$^4$=halo, alkyl, trifluoromethyl, etc.) the known diaminopyridines (*J. Med. Chem.* 1997, 40, 3679) of Type A are treated under cycloaddition conditions to afford the parent imidazo[1,2-a]pyridine skeletons B. Reductive amination with aldehydes yields compounds of Type C.

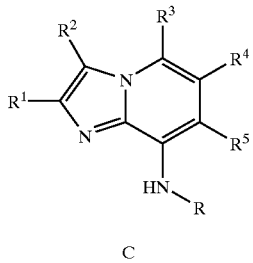

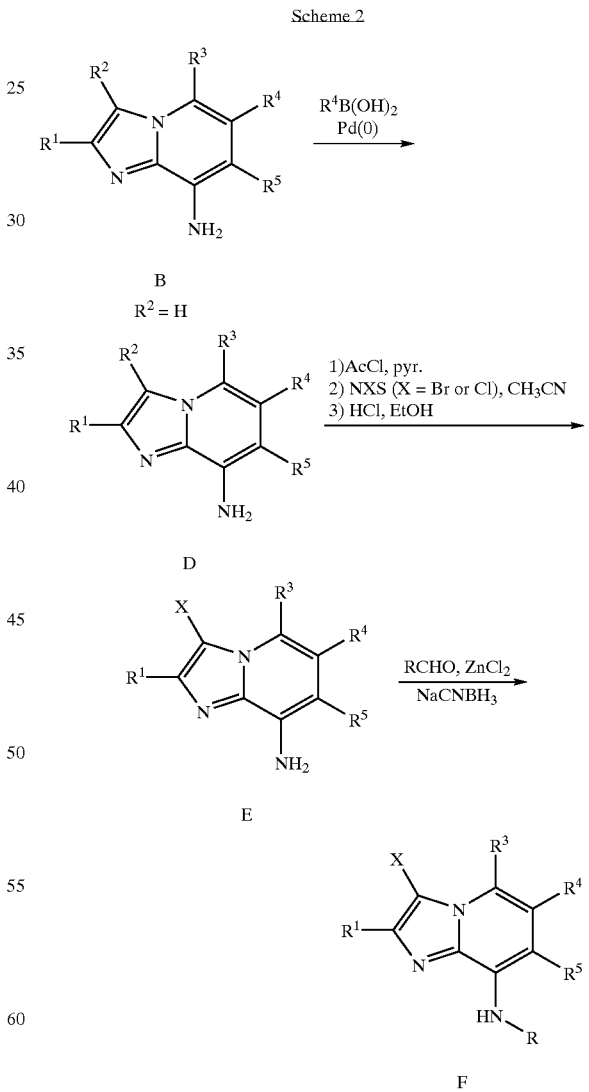

For more highly elaborated derivatives (R$^2$=Br, Cl; R$^4$=aryl or heteroaryl), the parent compound of Type B is treated under Suzuki coupling conditions to afford compounds of Type D. N-Acetylation followed by regioselective halogenation affords compounds of Type E. The intermediate is elaborated via reductive amination to afford compounds of Type F as described previously in Scheme 1.

Scheme 3

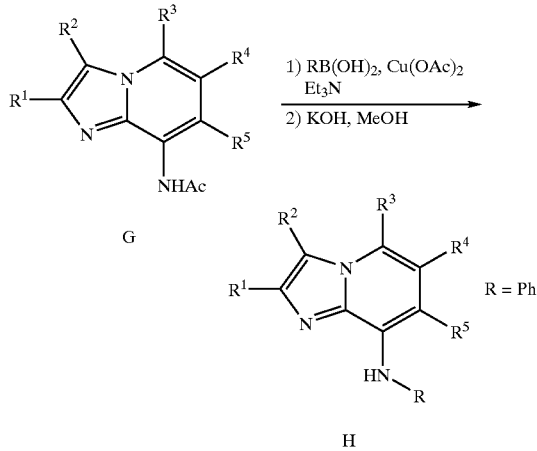

N-acylated derivatives of Type G are treated under arylation conditions followed by cleavage of the acetate under basic conditions to afford final products of type H.

Scheme 4

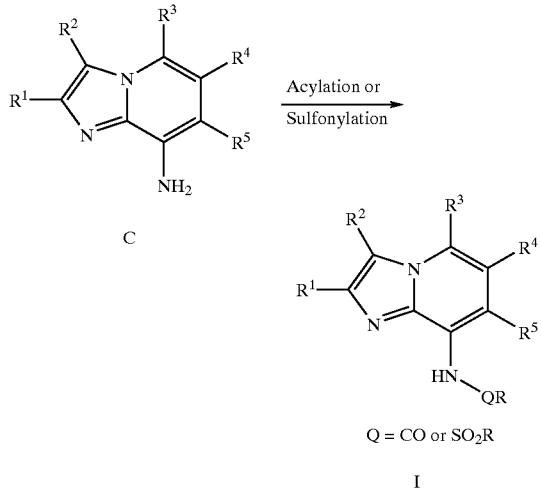

Treatment of aniline core structures of Type C under standard acylation or sulfonylation conditions affords the final products I.

Scheme 5

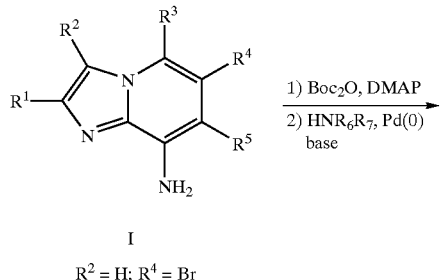

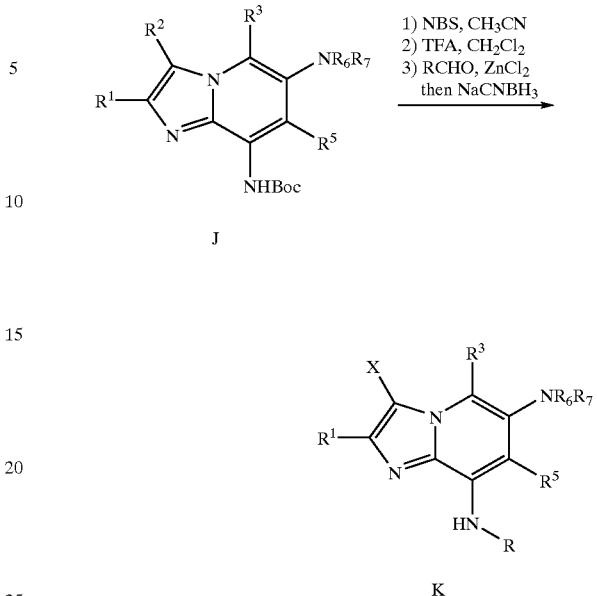

Nitrogen protection of aniline core I of Type I ($R^2$=H, $R^4$=Br) followed by palladium-mediated amination reaction affords the adduct J. In an analogous fashion to Scheme 2, bromination followed by deprotection and reductive amination affords the adducts of type K.

Preparative Example 10

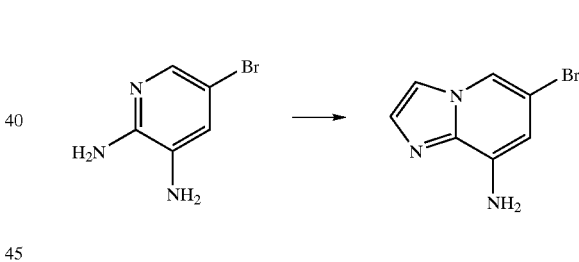

To a soln of bromoacetaldehyde diethyl acetal (2.37 mL, 15.4 mmol) in dioxane/$H_2O$ (2:1/15 mL) at rt was added conc. HCl (0.3 mL) and the mixture was refluxed for 30 min. The mixture was cooled to rt whereupon $NaHCO_3$ (2.6 g, 30.8 mmol) was carefully added followed by dropwise addition of diamino derivative (1.5 g, 7.7 mmol) in dioxane/$H_2O$ (2:1/15 mL). The resultant mixture was stirred at reflux for 14 h and was cooled to rt. The mixture was diluted with 1 M NaOH (30 mL) and was extracted with $CH_2Cl_2$ (3×35 mL). The organic layers were combined, washed with brine (1×20 mL), dried ($Na_2SO_4$), filtered and concentrated under reduced pressure to afford 1.5 g (92%) of the desired compound [M+H=214.0].

Preparative Examples 11, 12

Following the procedure set forth in Preparative Example 10 but by utilizing known diaminopyridines (*J. Med. Chem.* 1997, 40, 3679), the following imidazo[1,5-a]pyridine cores (Products) were prepared as indicated in Table 2.

TABLE 2

| Preparative Example | Pyridine | Product | 1. Yield (%) 2. MH+ |
|---|---|---|---|
| 11 | 5-chloro-2-amino-3-aminopyridine | 6-chloro-8-amino-imidazo[1,2-a]pyridine | 1. 73 2. 168.0 |
| 12 | 5-methyl-2-amino-3-aminopyridine | 6-methyl-8-amino-imidazo[1,2-a]pyridine | 1. 84 2. 148.0 |

Example 20

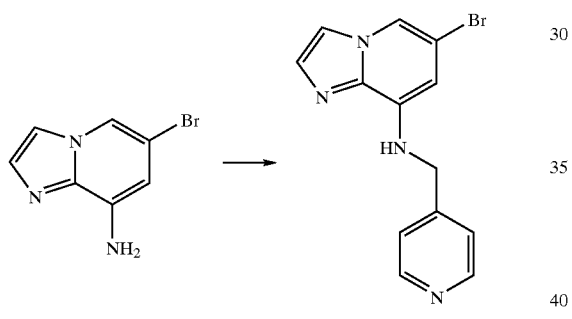

To a solution of aniline (0.10 g, 0.47 mmol) from Preparative Example 10 in MeOH (3 mL) at rt was added 4-pyridinecarboxyaldehyde (55 μL, 0.59 mmol) and ZnCl$_2$ (112 mg, 0.82 mmol). The resultant mixture was stirred for 1 h whereupon NaCNBH$_3$ (37 mg, 0.59 mmol) was added in one portion. The mixture was stirred at reflux for 14 h, cooled to rt, and concentrated under reduced pressure. The crude material was partitioned between CH$_2$Cl$_2$ (7 mL) and 2M NaOH (3 mL) and the layers were separated. The aqueous layer was extracted with CH$_2$Cl$_2$ (2×7 mL) and the organic layers were combined. The organic layer was dried (Na$_2$SO$_4$), filtered and concentrated under reduced pressure. The crude material was purified by prep TLC (6×1000 μM) using CH$_2$Cl$_2$/MeOH (20:1) as eluant to afford 52 mg (37%) of a red-brown solid [M+H=305.0]; mp 167–172° C.

Examples 21–26

Following the procedure set forth in Example 20 but using the prepared aniline derivatives (Preparative Examples 11 & 12) indicated in Table 3 and commercially available aldehydes, the substituted imidazo[1,2-a]pyridine adducts were prepared (Products).

TABLE 3

| Ex. | Prep Ex. Aniline | Aldehyde | Product | 1. Yield (%) 2. MH+ 3. mp (° C.) |
|---|---|---|---|---|
| 21 | 11 | benzaldehyde | product | 1. 73 2. 238.0 3. 135–137 |
| 22 | 11 | 4-pyridinecarboxaldehyde | product | 1. 57 2. 239.0 3. 131–133 |
| 23 | 11 | 3-pyridinecarboxaldehyde | product | 1. 68 2. 239.0 3. 131–133 |

TABLE 3-continued

| Ex. | Prep Ex. Aniline | Aldehyde | Product | 1. Yield (%) 2. MH+ 3. mp (° C.) |
|---|---|---|---|---|
| 24 | 12 | benzaldehyde | Cl-imidazopyridine-NHCH2Ph | 1. 95  2. 258.1  3. 119–122 |
| 25 | 12 | 4-pyridinecarboxaldehyde | Cl-imidazopyridine-NHCH2(4-pyridyl) | 1. 35  2. 259.0  3. 125–127 |
| 26 | 12 | 3-pyridinecarboxaldehyde | Cl-imidazopyridine-NHCH2(3-pyridyl) | 1. 55  2. 259.0  3. 127–130 |

Preparative Example 20

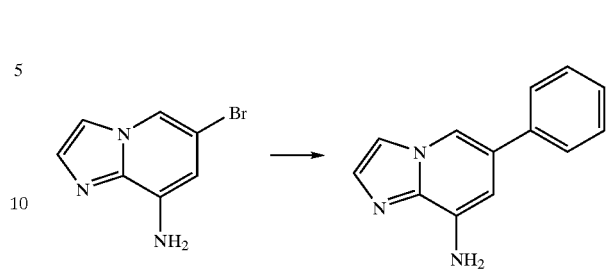

To a solution of bromo compound from Preparative Example 10 (1.0 g, 4.72 mmol) in DME/H$_2$O (4:1; 25 ml total) at rt was added PhB(OH)$_2$ (1.2 g, 9.4 mmol), K$_3$PO$_4$ (3.0 g, 14.2 mmol), and Pd(PPh$_3$)$_4$ (0.54 g, 0.47 mmol). The mixture was heated at reflux for 18 h and was cooled to rt. EtOAc (30 mL) and water (10 mL) were added and the layers were separated. The aqueous layer was extracted with EtOAc (3×30 mL) and the organic layers were combined. The organic layer was washed with brine (1×25 mL), dried (Na$_2$SO$_4$), filtered, and concentrated under reduced pressure to afford a brown oil. The crude product was purified by prep TLC (10×1000 μM) using CH$_2$Cl$_2$/MeOH (25:1) as eluant to afford 0.9 g (91%) of a brown solid [M+H=209.0].

Preparative Examples 21–25

Following the procedure set forth in Preparative Example 20 but by utilizing different boronic acid in the Suzuki coupling reaction with aniline from Preparative Example 10, the following aniline cores (Products) were prepared as indicated in Table 4.

TABLE 4

| Preparative Example | Boronic Acid | Product | 1. Yield (%) 2. MH+ |
|---|---|---|---|
| 21 | 2-chlorophenylboronic acid | 6-(2-chlorophenyl)imidazopyridine-NH2 | 1. 78  2. 244.0 |
| 22 | 2-trifluoromethylphenylboronic acid | 6-(2-trifluoromethylphenyl)imidazopyridine-NH2 | 1. 65  2. 278.0 |

TABLE 4-continued

| Preparative Example | Boronic Acid | Product | 1. Yield (%) 2. MH+ |
|---|---|---|---|
| 23 | 3-chlorophenylboronic acid | 6-(3-chlorophenyl)imidazo[1,2-a]pyridin-8-amine | 1. 87  2. 244.0 |
| 24 | 3-(trifluoromethyl)phenylboronic acid | 6-(3-(trifluoromethyl)phenyl)imidazo[1,2-a]pyridin-8-amine | 1. 86  2. 278.0 |
| 25 | (5-methylthiophen-2-yl)boronic acid | 6-(5-chlorothiophen-2-yl)imidazo[1,2-a]pyridin-8-amine | 1. 15  2. 250.0 |

Preparative Example 30

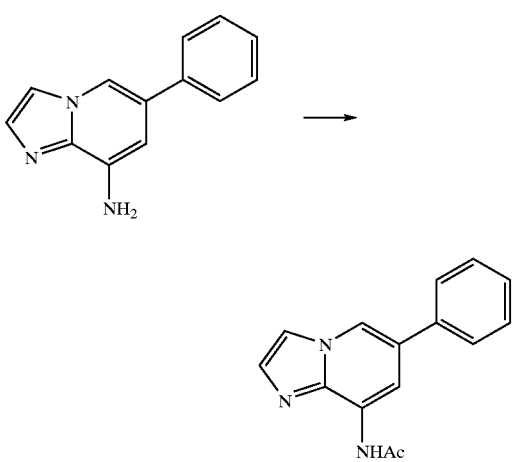

To a solution of aniline from Preparative Example 20 (0.12 g, 0.59 mmol) in CH$_2$Cl$_2$ (3 mL) at 0° C. was added pyridine (72 μL, 0.89 mmol) followed by dropwise addition of AcCl (50 μL, 0.71 mmol). The resulting heterogeneous mixture was stirred for 2 h at 0° C. and was concentrated under reduced pressure. The crude residue was suspended in CH$_2$Cl$_2$ (10 mL) and sat. aq. NaHCO$_3$ (5 mL) and the layers were separated. The aqueous layer was extracted with CH$_2$Cl$_2$ (2×10 mL) and the organic layers were combined. The organic layer was washed with brine (1×7 mL), dried (Na$_2$SO$_4$), filtered and concentrated under reduced pressure. The crude product was purified by prep TLC (4×1000 μM) using CH$_2$Cl$_2$/MeOH (25:1) as eluant to afford 0.12 g (78% yield) of a yellowish solid [M+H=252.0].

Preparative Examples 31–36

Following the procedure set forth in Preparative Example 30 but by utilizing the following aniline cores described in Preparative Examples 10, 21–25, the acylated derivatives (Products) were prepared as indicated in Table 5.

TABLE 5

| Preparative Example | Aniline | Product | 1. Yield (%) 2. MH+ |
|---|---|---|---|
| 31 | Prep. Ex. 21 | imidazo[1,2-a]pyridine with 2-chlorophenyl and NHAc | 1. 95 2. 286.0 |
| 32 | Prep. Ex. 22 | imidazo[1,2-a]pyridine with 2-CF₃-phenyl and NHAc | 1. 98 2. 320.1 |
| 33 | Prep. Ex. 23 | imidazo[1,2-a]pyridine with 3-chlorophenyl and NHAc | 1. 93 2. 286.0 |
| 34 | Prep. Ex. 24 | imidazo[1,2-a]pyridine with 3-CF₃-phenyl and NHAc | 1. 89 2. 320.1 |
| 35 | Prep. Ex. 25 | imidazo[1,2-a]pyridine with 5-chlorothiophen-2-yl and NHAc | 1. 76 2. 292.0 |
| 36 | Prep Ex. 10 | imidazo[1,2-a]pyridine with Br and NHAc | 1. 89 2. 256.0 |

Preparative Example 40

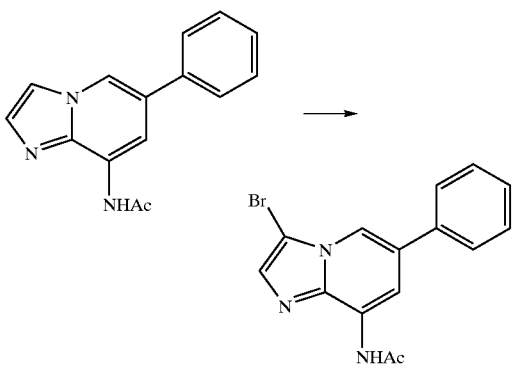

To a solution of acetate from Preparative Example 30 (0.12 g, 0.46 mmol) in CH$_3$CN (5 mL) at 0° C. was added NBS (73 mg, 0.41 mmol) in one portion to afford a heterogeneous mixture. The resulting solution was stirred for 1 h at 0° C. whereupon the reaction mixture was concentrated under reduced pressure. The crude material was purified by prep TLC (6×1000 μM) using CH$_2$Cl$_2$/MeOH (20:1) as eluant to afford 0.14 g (89%) of a yellow solid [M+H=330.1].

Preparative Examples 41–45

Following the procedure set forth in Preparative Example 40 but by utilizing the following aniline cores described in Preparative Examples 31–34, the 3-bromo derivatives (Products) were prepared as indicated in Table 6.

TABLE 6

| Preparative Example | Acetate | Product | 1. Yield (%) 2. MH$^+$ |
|---|---|---|---|
| 41 | Prep. Ex. 31 | | 1. 79 2. 366.1 |
| 42 | Prep. Ex. 32 | | 1. 72 2. 400.1 |
| 43 | Prep. Ex. 33 | | 1. 76 2. 366.1 |
| 44 | Prep. Ex. 34 | | 1. 89 2. 400.1 |

TABLE 6-continued

| Preparative Example | Acetate | Product | 1. Yield (%)<br>2. MH+ |
|---|---|---|---|
| 45 | Prep. Ex. 35 | ![structure with Cl-thiophene and NHAc] | 1. 98<br>2. 370.6 |

Preparative Example 50

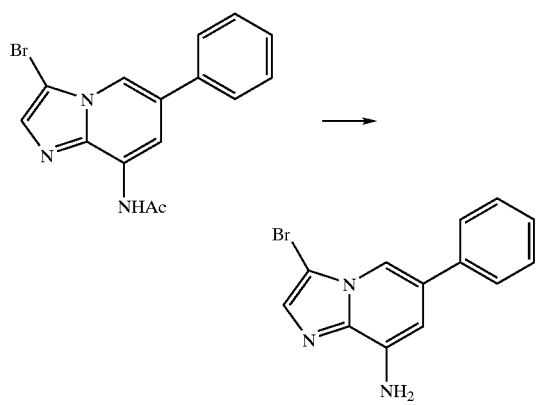

To a solution of 3-bromo derivative from Preparative Example 40 (0.14 g, 0.41 mmol) in EtOH (3 mL) was added conc. HCl (0.2 mL) and the mixture was refluxed for 4 h. The mixture was cooled to rt and was concentrated under reduced pressure. The crude product was partitioned between $CH_2Cl_2$ (7 mL) and sat. aq. $NaHCO_3$ (3 mL) and the layers were separated. The aqueous layer was extracted with $CH_2Cl_2$ (2×7 mL) and the organic layers were combined. The organic layer was dried ($Na_2SO_4$), filtered and concentrated under reduced pressure to afford 0.11 g (93% yield) of an off-white solid [M+H=288.0]. This material was carried on without further purification.

Preparative Examples 51–54

Following the procedure set forth in Preparative Example 50 but by utilizing the following 3-bromo acetylated aniline cores described in Preparative Examples 41–44, the aniline derivatives (Products) were prepared as indicated in Table 7.

TABLE 7

| Preparative Example | 3-Bromo Derivative | Product | 1. Yield (%)<br>2. M + H |
|---|---|---|---|
| 51 | Prep. Ex. 41 | ![structure with Br, Cl-phenyl, NH2] | 1. 88<br>2. 322.1 |
| 52 | Prep. Ex. 42 | ![structure with Br, CF3-phenyl, NH2] | 1. 91<br>2. 358.1 |
| 53 | Prep. Ex. 43 | ![structure with Br, Cl-phenyl, NH2] | 1. 99<br>2. 324.1 |

TABLE 7-continued

| Preparative Example | 3-Bromo Derivative | Product | 1. Yield (%) 2. M + H |
|---|---|---|---|
| 54 | Prep. Ex. 44 | (structure) | 1. 94 2. 356.1 |

Example 100

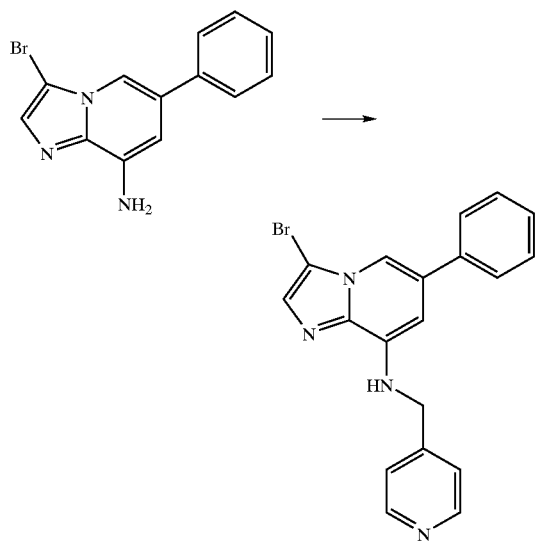

To a solution of aniline (0.11 g, 0.36 mmol) from Preparative Example 50 in MeOH (4 mL) at rt was added 4-pyridinecarboxyaldehyde (44 μL, 0.46 mmol) and $ZnCl_2$ (87 mg, 0.64 mmol). The resultant mixture was stirred for 1 h whereupon $NaCNBH_3$ (29 mg, 0.46 mmol) was added in one portion. The mixture was stirred at reflux for 14 h, cooled to rt, and concentrated under reduced pressure. The crude material was partitioned between $CH_2Cl_2$ (7 mL) and 2M NaOH (3 mL) and the layers were separated. The aqueous layer was extracted with $CH_2Cl_2$ (2×7 mL) and the organic layers were combined. The organic layer was dried ($Na_2SO_4$), filtered and concentrated under reduced pressure. The crude material was purified by prep TLC (6×1000 μM) using $CH_2Cl_2$/MeOH (20:1) as eluant to afford 0.07 g (49%) of a brown solid [M+H=379.1]; mp 167–172° C.

Examples 101–118

Following the procedure set forth in Example 100 but using the prepared aniline derivatives (Preparative Example 50–54) indicated in Table 8 and commercially available aldehydes, the substituted imidazo[1,2-a]pyridine adducts were prepared (Products).

TABLE 8

| Ex. | Prep Ex. Aniline | Aldehyde | Product | 1. Yield (%) 2. M + H 3. mp (° C.) |
|---|---|---|---|---|
| 101 | 50 | (structure) | (structure) | 1. 84 2. 379.1 3. 190–192 |

TABLE 8-continued

| Ex. | Prep Ex. Aniline | Aldehyde | Product | 1. Yield (%)<br>2. M + H<br>3. mp (° C.) |
|---|---|---|---|---|
| 102 | 50 | benzaldehyde | 3-bromo-6-phenyl-N-benzyl-imidazo[1,2-a]pyridin-8-amine | 1. 85<br>2. 380.1<br>3. 160–162 |
| 103 | 50 | thiophene-2-carbaldehyde | 3-bromo-6-phenyl-N-(thiophen-2-ylmethyl)imidazo[1,2-a]pyridin-8-amine | 1. 88<br>2. 386.1<br>3. 186–189 |
| 104 | 50 | furan-2-carbaldehyde | 3-bromo-6-phenyl-N-(furan-2-ylmethyl)imidazo[1,2-a]pyridin-8-amine | 1. 89<br>2. 370.1<br>3. 179–181 |
| 105 | 50 | pyrimidine-5-carbaldehyde | 3-bromo-6-phenyl-N-(pyrimidin-5-ylmethyl)imidazo[1,2-a]pyridin-8-amine | 1. 53<br>2. 382.1<br>3. 157–159 |

TABLE 8-continued

| Ex. | Prep Ex. Aniline | Aldehyde | Product | 1. Yield (%) 2. M + H 3. mp (° C.) |
|---|---|---|---|---|
| 106 | 50 | pyrimidine-CHO with NHBoc | 3-Br-6-phenyl-imidazo[1,2-a]pyridine-8-yl-NH-CH2-(NHBoc-pyrimidine) | 1. 35 2. 495.1 3. 198–200 |
| 107 | 50 | pyridine N-oxide-4-CHO | 3-Br-6-phenyl-imidazo[1,2-a]pyridine-8-yl-NH-CH2-(pyridine N-oxide) | 1. 69 2. 431.1 3. 222–225 |
| 108 | 51 | 4-pyridinecarboxaldehyde | 3-Br-6-(2-Cl-phenyl)-imidazo[1,2-a]pyridine-8-yl-NH-CH2-(4-pyridyl) | 1. 47 2. 415.1 3. 199–201 |
| 109 | 51 | 3-pyridinecarboxaldehyde | 3-Br-6-(2-Cl-phenyl)-imidazo[1,2-a]pyridine-8-yl-NH-CH2-(3-pyridyl) | 1. 87 2. 415.1 3. 196–199 |

TABLE 8-continued

| Ex. | Prep Ex. Aniline | Aldehyde | Product | 1. Yield (%) 2. M + H 3. mp (° C.) |
|---|---|---|---|---|
| 109 | 51 | pyrimidine-5-carbaldehyde | 3-bromo-6-(2-chlorophenyl)-N-(pyrimidin-5-ylmethyl)imidazo[1,2-a]pyridin-8-amine | 1. 43 2. 416.1 3. 206–208 |
| 111 | 51 | 2-aminopyrimidine-5-carbaldehyde | N-((2-aminopyrimidin-5-yl)methyl)-3-bromo-6-(2-chlorophenyl)imidazo[1,2-a]pyridin-8-amine | 1. 40 2. 431.1 3. 211–213 |
| 112 | 51 | thiazole-2-carbaldehyde | 3-bromo-6-(2-chlorophenyl)-N-(thiazol-2-ylmethyl)imidazo[1,2-a]pyridin-8-amine | 1. 90 2. 421.1 3. 200–202 |
| 113 | 52 | isonicotinaldehyde | 3-bromo-N-(pyridin-4-ylmethyl)-6-(2-(trifluoromethyl)phenyl)imidazo[1,2-a]pyridin-8-amine | 1. 60 2. 449.1 3. 194–196 |

TABLE 8-continued
| Ex. | Prep Ex. Aniline | Aldehyde | Product | 1. Yield (%)<br>2. M + H<br>3. mp (° C.) |
|---|---|---|---|---|
| 114 | 52 | 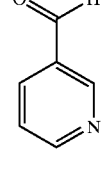 | 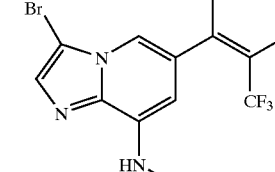 | 1. 95<br>2. 447.0<br>3. 192–195 |
| 115 | 53 | 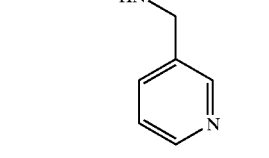 | 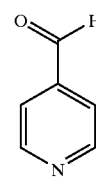 | 1. 83<br>2. 415.1<br>3. 188–190 |
| 116 | 53 | 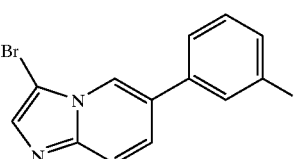 | 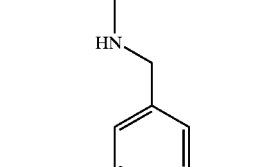 | 1. 42<br>2. 413.0<br>3. 191–194 |
| 117 | 54 | 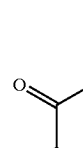 | 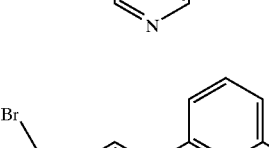 | 1. 44<br>2. 449.1 |

TABLE 8-continued

| Ex. | Prep Ex. Aniline | Aldehyde | Product | 1. Yield (%) 2. M + H 3. mp (° C.) |
|---|---|---|---|---|
| 118 | 54 | (nicotinaldehyde) | 3-bromo-6-[3-(trifluoromethyl)phenyl]-N-(pyridin-3-ylmethyl)imidazo[1,2-a]pyridin-8-amine | 1. 82 2. 449.1 3. 188–190 |
| 119 | 55 | (nicotinaldehyde) | 3-bromo-6-(5-chlorothiophen-2-yl)-N-(pyridin-3-ylmethyl)imidazo[1,2-a]pyridin-8-amine | 1. 36 2. 421 3. 125–127 |
| 120 | 55 | (pyrimidine-5-carbaldehyde) | 3-bromo-6-(5-chlorothiophen-2-yl)-N-(pyrimidin-5-ylmethyl)imidazo[1,2-a]pyridin-8-amine | 1. 22 2. 422 3. 118–121 |
| 121 | 51 | (6-(trifluoromethyl)nicotinaldehyde) | 3-bromo-6-(2-chlorophenyl)-N-{[6-(trifluoromethyl)pyridin-3-yl]methyl}imidazo[1,2-a]pyridin-8-amine | 1. 83 2. 483 3. 106–108 |

TABLE 8-continued

| Ex. | Prep Ex. Aniline | Aldehyde | Product | 1. Yield (%) 2. M + H 3. mp (° C.) |
|---|---|---|---|---|
| 122 | 51 | 2-phenylpyrimidine-5-carbaldehyde | 3-bromo-6-(2-chlorophenyl)-N-((2-phenylpyrimidin-5-yl)methyl)imidazo[1,2-a]pyridin-8-amine | 1. 79 2. 492 3. 188–191 |
| 123 | 51 | 5-chlorothiophene-2-carbaldehyde | 3-bromo-6-(2-chlorophenyl)-N-((5-chlorothiophen-2-yl)methyl)imidazo[1,2-a]pyridin-8-amine | 1. 98 2. 454 3. 197–200 |
| 124 | 51 | 5-(phenylsulfonyl)thiazole-2-carbaldehyde | 3-bromo-6-(2-chlorophenyl)-N-((5-(phenylsulfonyl)thiazol-2-yl)methyl)imidazo[1,2-a]pyridin-8-amine | 1. 22 2. 561 3. 211–213 |

Preparative Example 60

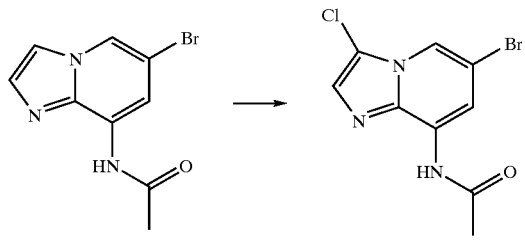

To a solution of acetate (100 mg, 0.39 mmol) from Preparative Example 36 in CH$_3$CN (4 mL) at 0° C. was added NCS (47 mg, 0.35 mmol) in one portion. The mixture was warmed to rt and heated to reflux and stirred for 1 h. The mixture was cooled to rt and was concentrated under reduced pressure. The crude material was purified by prep TLC (6×1000 μM) using CH$_2$Cl$_2$/MeOH (22:1) as eluent to afford 96 mg (86%) of a white solid [M+H=290.0].

Preparative Example 65

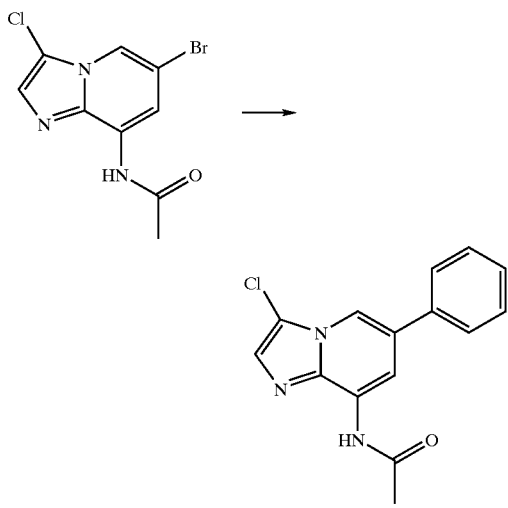

Following the procedure set forth in Preparative Example 20 but by utilizing the acetate derivative from Preparative Example 60, the final target was prepared in 79% yield as and orange solid [M+H=286.0].

Preparative Example 70

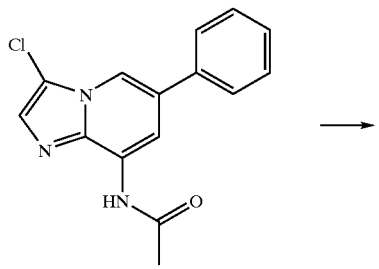

-continued

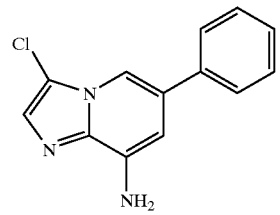

Following the procedure set forth in Preparative Example 50 but by utilizing the acetate derivative from Preparative Example 65, the final target was prepared in 98% yield. [M+H=244.0].

Example 200

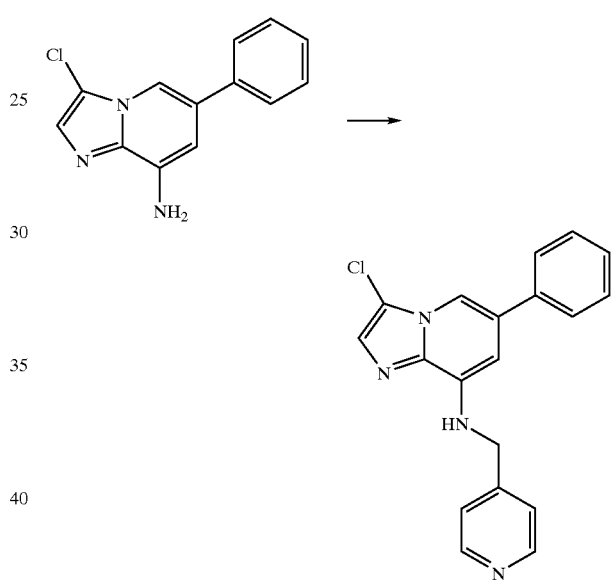

Following the procedure set forth in Example 100 except using the prepared aniline from Preparative Example 70 with 4-pyridylcarboxaldehyde, the final product indicated in Table 9 and commercially available aldehydes, the substituted imidazo[1,2-a]pyridine adduct was prepared as a light yellow solid in 35% yield. mp 202–205° C.; [M+H=335.0].

Preparative Example 80

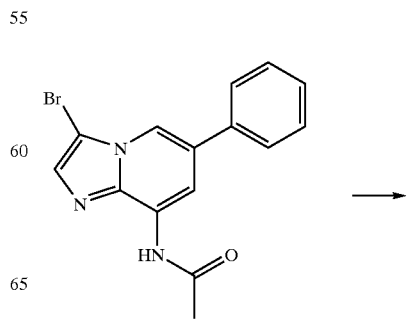

-continued

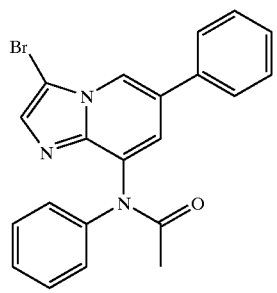

To solution of acetate (30 mg, 0.09 mmol) from Preparative Example 40 in. CH$_2$Cl$_2$ (2 mL) at rt was added Cu(OAc)$_2$ (16 mg, 0.09 mmol), PhB(OH)$_2$ (22 mg, 0.18 mmol) and Et$_3$N (25 µL, 0.18 mmol). The mixture was stirred for 24 h at rt and was concentrated under reduced pressure. The crude material was purified by prep TLC (4×1000 µM) using CH$_2$Cl$_2$/MeOH (25:1) as eluant to afford 15 mg (41%) of product [M+H=408.1].

Preparative Examples 81–82

Following the procedure set forth in Preparative Example 80 but by utilizing the specified acetylated aniline cores described in Preparative Examples 43,44 the aniline derivatives (Products) were prepared as indicated in Table 10.

Example 200

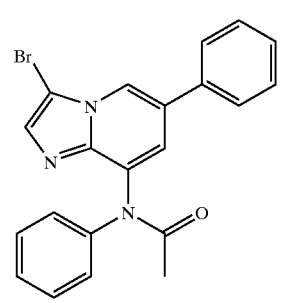 

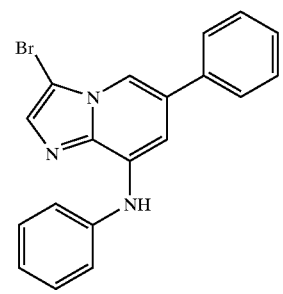

To a solution of the acetate (15 mg, 0.037 mmol) in MeOH/H$_2$O (1:1; 2 mL total) at rt was added KOH (42 mg, 0.74 mmol) in one portion. The mixture was stirred at reflux for 8 h, cooled to rt, and concentrated to dryness. The resultant residue was partitioned between H$_2$O (1 mL) and

TABLE 10

| Preparative Example | Acetate | Product | 1. Yield (%) 2. MH+ |
|---|---|---|---|
| 81 | Prep. Ex. 43 | ![structure] | 1. 21 2. 442.1 |
| 82 | Prep. Ex. 44 | ![structure] | 1. 32 2. 474.1 |

CH₂Cl₂ (3 mL) and the layers were separated. The aqueous layer was extracted with CH₂Cl₂ (2×3 mL) and the organic layers were combined. The organic layer was dried (Na₂SO₄), filtered, and concentrated under reduced pressure. The crude material was purified by prep TLC (4×1000 μM) using hexanes/EtOAc (5:1) as eluant to afford 9 mg (67%) of red-brown semisolid. [M+H=366.1].

Example 201

Following the procedure set forth in Example 200 but using the prepared acetate derivative (Preparative Example 50) indicated in Table 11 available, the N8 phenyl substituted imidazo[1,2-a]pyridine adducts were prepared (Products).

TABLE 11

| Ex. | Prep Ex. Aniline | Product | 1. Yield (%) 2. MH⁺ 3. mp (° C.) |
|---|---|---|---|
| 201 | 82 | | 1. 78 2. 434.1 3. 152–153 |

Example 300

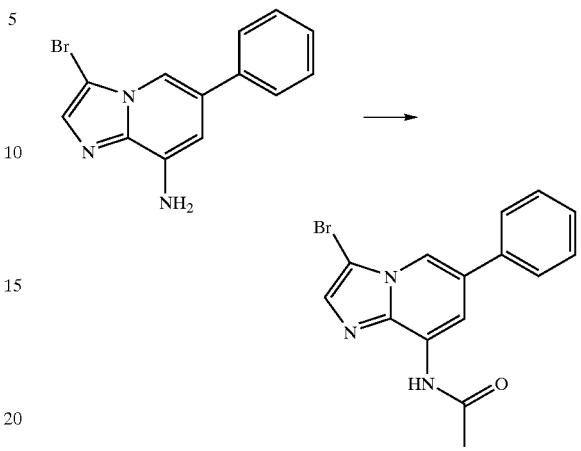

Following the procedure set forth in Example 30 except using the prepared aniline from Preparative Example 50, the acylated derivative was prepared in 89% yield as a yellow solid, mp. 92–96° C.; [M+H=332.1].

Examples 301–304

Following the procedure set forth in Example 300 but using various aniline cores as indicated in Table 12 reacting with designated acid chlorides, the N8 acylated substituted imidazo[1,2-a]pyridine adducts are prepared (Products).

TABLE 12

| Ex. | Prep Ex. Aniline | Acid Chloride | Product |
|---|---|---|---|
| 301 | (Prep Ex. 50) | | |
| 302 | | | |

TABLE 12-continued

| Ex. | Prep Ex. Aniline | Acid Chloride | Product |
|---|---|---|---|
| 303 | | | |
| 304 | | | |

Example 400

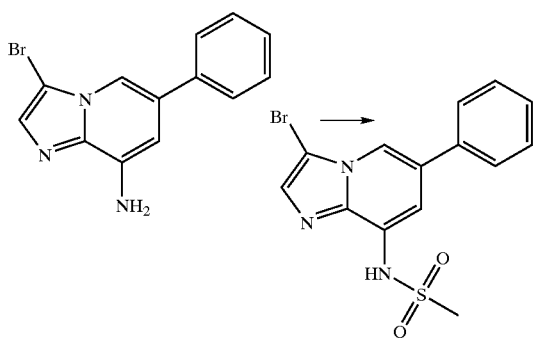

The core aniline from Preparative Example 50 is reacted with methanesulfonyl chloride in the presence of pyridine to afford the desired product.

Examples 401–404

Following the procedure set forth in Example 400 but using various aniline cores as indicated in Table 13 reacting with designated acid chlorides, the N8 sulfonylated substituted imidazo[1,2-a]pyridine adducts are prepared (Products).

TABLE 13

| Ex. | Prep Ex. Aniline | Sulfonyl Chloride | Product |
|---|---|---|---|
| 401 | (Prep Ex. 50) | | |

TABLE 13-continued
| Ex. | Prep Ex. Aniline | Sulfonyl Chloride | Product |
|---|---|---|---|
| 402 | 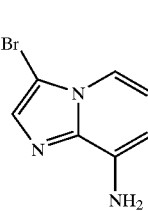 | 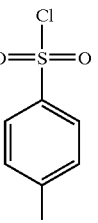 | 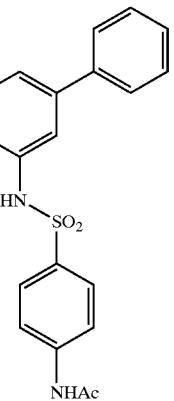 |
| 403 | 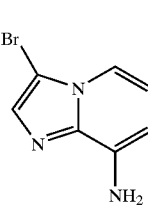 | 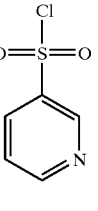 | 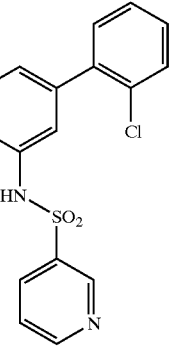 |
| 404 | 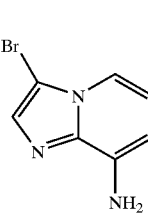 | 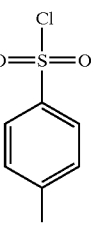 | 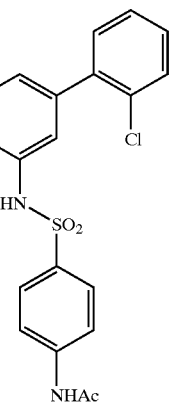 |

Preparative Example 90

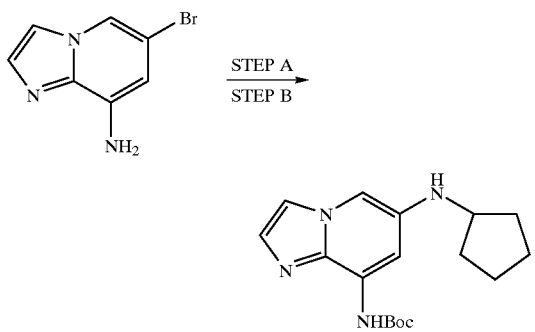

Step A:
Treatment of aniline derivative from Preparative Example 10 under standard conditions (Boc$_2$O, Et$_3$N, DMAP) affords the corresponding carbamate derivative.

Step B:
Treatment of the derivative from Step A under standard amination conditions (Pd(OAc)$_2$, BINAP, Cs$_2$CO$_3$) and by employing cyclopentylamine affords the desired cyclopentyl amine derivative.

Preparative Examples 91–100

Following the procedure set forth in Preparative Example 90 but by utilizing the carbamate described in Preparative Examples 90 Step A with various amines, the amino derivatives (Products) are prepared as indicated in Table 14.

Preparative Example 101

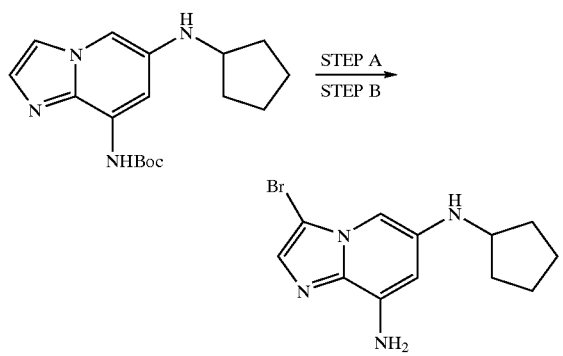

Step A:
Treatment of Boc derivative from Preparative Example 90 according to the procedure set forth in Preparative Example 40 affords the 3-bromo adduct.

Step B:
Treatment of the product from STEP A under acidic conditions (HCl) according to the procedure set forth in Preparative Example 50 affords the aniline derivative.

Preparative Examples 102–111

Following the procedure set forth in Preparative Example 100 but by utilizing the carbamate derivatives described in Preparative Examples 91–95, the amine derivatives (Products) are prepared as indicated in Table 15.

TABLE 15

| Preparative Example | Carbamate | Product |
|---|---|---|
| 102 | 91 | (structure) |
| 103 | 92 | (structure) |
| 104 | 93 | (structure) |
| 105 | 94 | (structure) |
| 106 | 95 | (structure) |
| 107 | 96 | (structure) |
| 108 | 97 | (structure) |
| 109 | 98 | (structure) |
| 110 | 99 | (structure) |
| 111 | 100 | (structure) |

Example 500

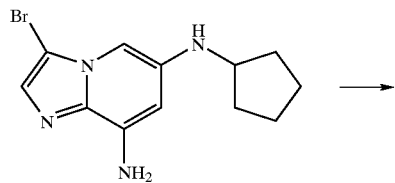

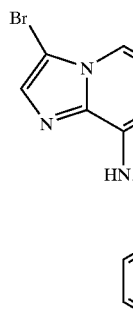

Treatment of aniline from Preparative Example 100 with 3-pyridine carboxaldehyde according to the procedure outlined in Example 100 affords the title compound.

Examples 501–510

Following the procedure set forth in Example 500 but by utilizing the aniline derivatives described in Preparative Examples 101–105, the final adducts (Products) can be prepared as indicated in Table 16.

TABLE 16

| Example | Aniline (Prep. Ex.) | Product |
|---|---|---|
| 501 | 102 | |
| 502 | 103 | |
| 503 | 104 | |
| 504 | 105 | |
| 505 | 106 | |
| 506 | 107 | |

TABLE 16-continued

| Example | Aniline (Prep. Ex.) | Product |
|---|---|---|
| 507 | 108 | 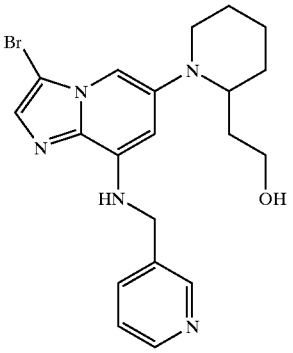 |
| 508 | 109 | 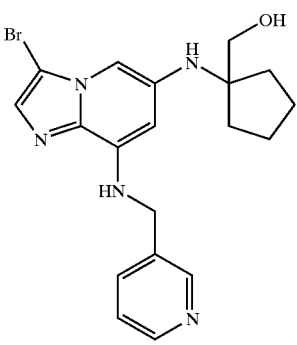 |
| 509 | 110 | 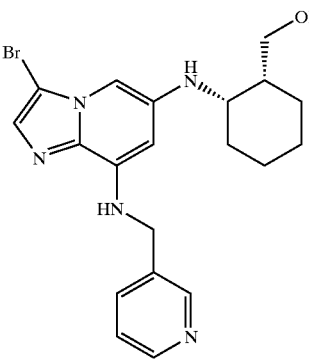 |
| 510 | 111 | 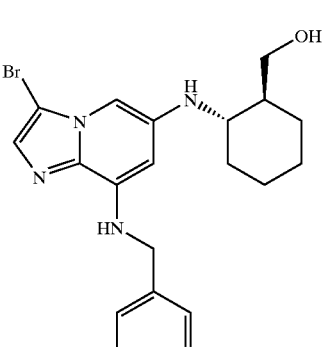 |

Assay:

BACULOVIRUS CONSTRUCTIONS: Cyclin E was cloned into pVL1393. (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YD-VPDYAS). The expressed protein was approximately 34 kDa in size.

ENZYME PRODUCTION: Recombinant baculoviruses expressing cyclin E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 ml of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed overnight in 2 liters of kinase buffer containing 50 mM Tris pH 8.0, 1 mM DTT, 10 mM $MgCl_2$, 100 uM sodium orthovanadate and 20% glycerol. Enzyme was stored in aliquots at −70° C.

IN VITRO KINASE ASSAY: Cyclin E/CDK2 kinase assays were performed in low protein binding 96-well plates (Corning Inc, Corning, N.Y.). Enzyme was diluted to a final concentration of 50 μg/ml in kinase buffer containing 50 mM Tris pH 8.0, 10 mM $MgCl_2$, 1 mM DTT, and 0.1 mM sodium orthovanadate. The substrate used in these reactions was a biotinylated peptide derived from Histone H1 (from Amersham, UK). The substrate was thawed on ice and diluted to 2 μM in kinase buffer. Compounds were diluted in 10% DMSO to desirable concentrations. For each kinase reaction, 20 μl of the 50 μg/ml enzyme solution (1 μg of enzyme) and 20 μl of the 2 μM substrate solution were mixed, then combined with 10 μl of diluted compound in each well for testing. The kinase reaction was started by addition of 50 μl of 2 μM ATP and 0.1 μCi of 33P-ATP (from Amersham, UK). The reaction was allowed to run for 1 hour at room temperature. The reaction was stopped by adding 200 μl of stop buffer containing 0.1% Triton X-100, 1 mM ATP, 5 mM EDTA, and 5 mg/ml streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ DETERMINATION: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis. The thus-obtained $IC_{50}$ values for some representative compounds of the invention are shown in Table 17.

TABLE 17

| Examples | CDK2 IC$_{50}$ ($\mu$M) |
|---|---|
| 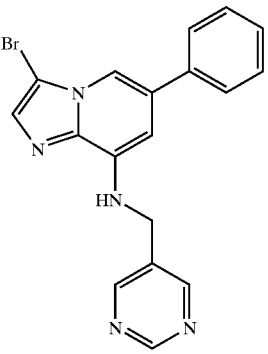 | 0.12 |
| 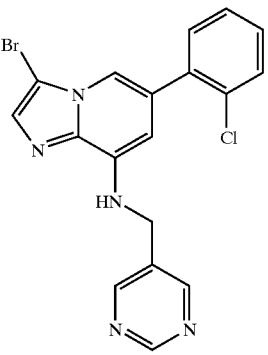 | 0.036 |
| 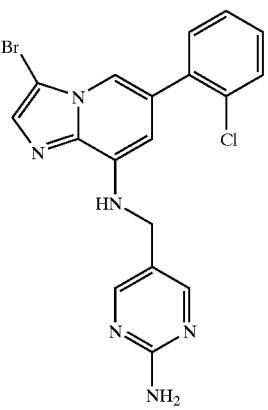 | 0.076 |

As demonstrated above by the assay values, the compounds of the present invention exhibit excellent CDK inhibitory properties.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural formula:

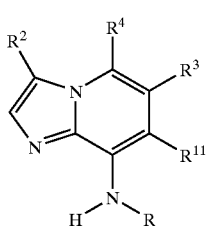

Formula III or a pharmaceutically acceptable salt or solvate thereof, wherein:

wherein R is unsubstituted phenyl, unsubstituted pyridyl or unsubstituted pyrimidinyl $R^2$ is selected from the group consisting of $R^9$, alkyl, aryl, arylalkyl, heteroaryl, heteroarylalkyl, heterocyclyl, heterocyclylalkyl, alkenyl, alkynyl, cycloalkyl, —CF$_3$, —C(O)R$^7$, alkyl substituted with 1–6 R$^9$ groups which groups can be the same or different with each R$^9$ being independently selected,

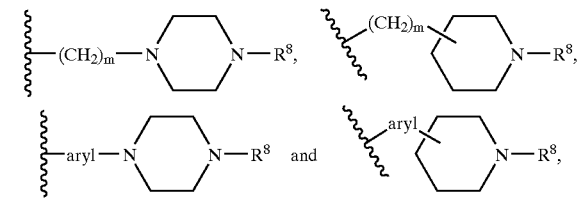

wherein each of said aryl, heteroaryl, arylalkyl and heterocyclyl can be unsubstituted or optionally independently substituted with one or more moieties which can be the same or different, each moiety being independently selected from the group consisting of halogen, alkyl, cycloalkyl, CF$_3$, CN, —OCF$_3$, —OR$^6$, —C(O)R$^7$, —NR$^5$R$^7$, —C(O)OR$^6$, —C(O)NR$^5$R$^6$, —SR$^6$, —S(O$_2$)R$^7$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

$R^3$ is selected from the group consisting of halogen, —NR$^5$R$^6$, cycloalkyl, aryl, heteroaryl, heteroarylalkyl, heterocyclyl, heterocyclylalkyl, alkynyl, alkenyl, —(CHR$^5$)$_n$-aryl, —(CHR$^5$)$_n$-heteroaryl, —(CHR$^5$)$_n$—OR$^6$, —S(O$_{2)R}$$^6$, —S(O$_2$)NR$^5$R$^6$, —CH(aryl)$_2$, —(CH$_2$)$_m$—NR$^8$,

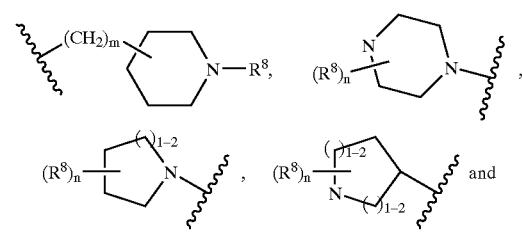

-continued

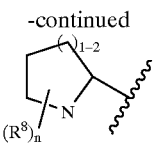

wherein each of said aryl, arylalkyl, cycloalkyl, heteroaryl, heteroarylalkyl, heterocyclyl and heterocyclylalkyl for $R^3$ and the heterocyclyl moieties whose structures are shown immediately above for $R^3$ can be unsubstituted or optionally independently substituted with one or more moieties which moieties can be the same or different, each moiety being independently selected from the group consisting of halogen, alkyl, aryl, cycloalkyl, $CF_3$, CN, —$OCF_3$, —$OR^5$, —$C(R^4R^5)_nOR^5$, —$NR^5R^6$, —$C(R^4R^5)_nNR^5R^6$, —$C(O_2)R^5$, —$C(O)R^5$, —$C(O)NR^5R^6$, —$SR^6$, —$S(O_2)R^6$, —$S(O_2)NR^5R^6$, —$N(R^5)S(O_2)R^7$, —$N(R^5)C(O)R^7$ and —$N(R^5)C(O)NR^5R^6$;

$R^4$ is selected from the group consisting of H, halogen, $CF_3$, alkyl, cycloalkyl, aryl, heteroaryl, heteroarylalkyl, heterocyclyl, heterocyclylalkyl, alkynyl, alkenyl, —$(CHR^5)_n$-aryl, —$(CHR^5)_n$-heteroaryl, —$(CHR^5)_n$—$OR^6$, —$S(O_2)R^6$, —$C(O)R^6$, —$S(O_2)NR^5R^6$, —$C(O)OR^6$, —$C(O)NR^5R^6$, cycloalkyl, —$CH(aryl)_2$, —$(CH_2)_m$—$NR^8$, and

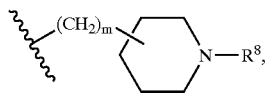

and wherein each of said aryl, alkyl, cycloalkyl, heteroaryl, heteroarylalkyl, heterocyclyl and heterocyclylalkyl can be unsubstituted or optionally substituted with one or more moieties which can be the same or different, each moiety being independently selected from the group consisting of halogen, alkyl, aryl, cycloalkyl, $CF_3$, CN, —$OCF_3$, —$OR^5$, —$NR^5R^6$, —$C(O_2)R^5$, —$C(O)NR^5R^6$, —$SR^6$ and —$S(O_2)R^6$;

$R^5$ is H, alkyl or aryl;

$R^6$ is selected from the group consisting of H, alkyl, aryl, heteroaryl, arylalkyl, cycloalkyl, heteroarylalkyl, heterocyclyl and heterocyclylalkyl, wherein each of said alkyl, aryl, heteroaryl, arylalkyl, cycloalkyl, heteroarylalkyl, heterocyclyl and heterocyclylalkyl can be unsubstituted or optionally independently substituted with one or more moieties which can be the same or different, each moiety being independently selected from the group consisting of halogen, alkyl, aryl, cycloalkyl, heterocyclylalkyl, $CF_3$, $OCF_3$, CN, —$OR^5$, —$NR^5R^{10}$, —$N(R^5)Boc$, —$C(R^4R^5)OR^5$, —$C(O)R^6$, —$C(O)OR^5$, —$C(O)NR^5R^{10}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocycloalkyl, $CF_3$, $OCF_3$, CN, —$OR^5$, —$NR^4R^5$, —$N(R^5)Boc$, —$(CR^4R^5)_nOR^5$, —$C(O_2)R^5$, —$C(O)NR^4R^5$, —$C(O)R^5$, —$SO_3H$, —$SR^5$, —$S(O_2)R^7$, —$S(O_2)NR^4R^5$, —$N(R^5)S(O_2)R^7$, —$N(R^5)C(O)R^7$ and —$N(R^5)C(O)NR^4R^5$;

or optionally (i) $R^5$ and $R^{10}$ in the moiety —$NR^5R^{10}$, or (ii) $R^5$ and $R^6$ in the moiety —$NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, heteroaryl, arylalkyl and heteroarylalkyl wherein each of said alkyl, cycloalkyl, heteroarylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$CH_2OR^5$, —$C(O_2)R^5$, —$C(O)NR^5R^{10}$, —$C(O)R^5$, —$SR^{10}$, —$S(O_2)R^{10}$, —$S(O_2)NR^5R^{10}$, —$N(R^5)S(O_2)R^{10}$, —$N(R^5)C(O)R^{10}$ and —$N(R^5)C(O)NR^5R^{10}$;

$R^8$ is selected from the group consisting of $R^6$, —$C(O)NR^5R^{10}$, —$S(O_2)NR^5R^{10}$, —$C(O)R^7$, —$C(O)OR^6$ and —$S(O_2)R^7$;

$R^9$ is selected from the group consisting of halogen, CN, $NR^5R^{10}$, —$C(O)OR^6$, —$C(O)NR^5R^{10}$, —$OR^6$, —$C(O)R^7$, —$SR^6$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{11}$ is H, alkyl or aryl;

m is 0 to 4; and n is 1–4.

2. The compound of claim 1, wherein R is pyridylmethyl whose pyridyl is unsubstituted or optionally substituted with one or more moieties selected from the group consisting of F, Cl, Br, CN, —$NH_2$, —$N(H)C(O)CH_3$ and $CF_3$.

3. The compound of claim 2, wherein said pyridyl is 2-pyridyl, 3-pyridyl or 4-pyridyl.

4. The compound of claim 1, wherein R is phenyl, pyridyl or pyrimidinyl each of which is substituted with one or more moieties which can be the same or different, each being independently selected from the group consisting of Cl, Br, —$NH_2$, —$N(H)C(O)CH_3$ or —$CF_3$.

5. The compound of claim 1, wherein $R^2$ is F, Cl, Br, I, hydroxyalkyl, alkoxyalkyl, or lower alkyl.

6. The compound of claim 5, wherein $R^2$ is Br, I, —$CH_2OH$, —$CH_2OCH_3$, or methyl.

7. The compound of claim 1, wherein $R^3$ is aryl, —$NR^5R^6$,

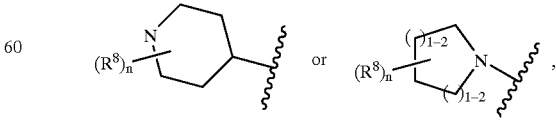

wherein said alkyl and aryl and the heterocyclyl moieties shown immediately above for $R^3$ can be unsubstituted or optionally independently substituted with one or more moieties (in addition to any R⁸) which can be the same or different, each moiety being independently selected from the group consisting of F, Cl, Br, $CF_3$, lower alkyl, hydroxyalkyl, alkoxy, —$S(O_2)R^6$, and CN.

8. The compound of claim 1, wherein $R^4$ is H, alkyl or aryl, wherein said alkyl or aryl can be unsubstituted or optionally independently substituted with one or more moieties which can be the same or different, each moiety being independently selected from the group consisting of F, Cl, Br, $CF_3$, lower alkyl, hydroxyalkyl, alkoxy, —$S(O_2)R^6$, and CN.

9. The compound of claim 1, wherein $R^5$ is H.
10. The compound of claim 1, wherein $R^{11}$ is H.
11. The compound of claim 1, wherein m is 0.
12. The compound of claim 1, wherein n is 1.
13. A compound of the formula:

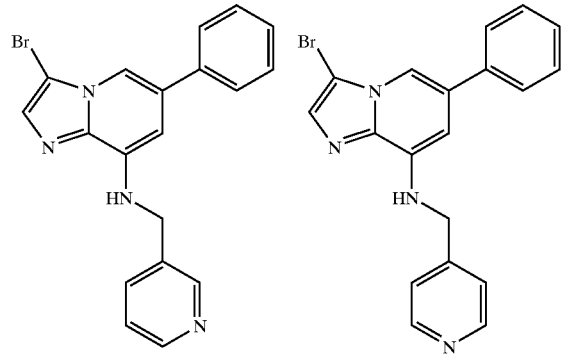
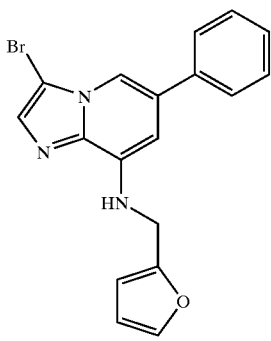
-continued
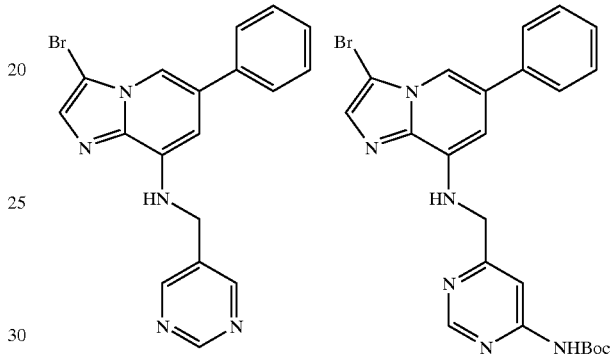
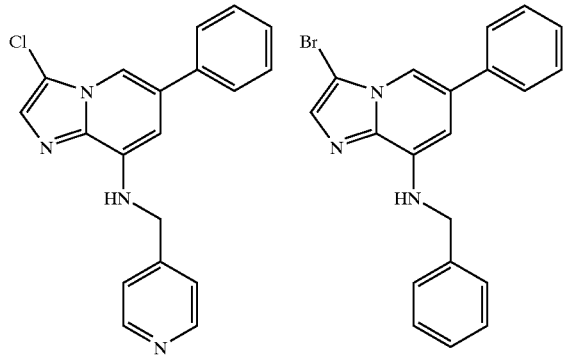
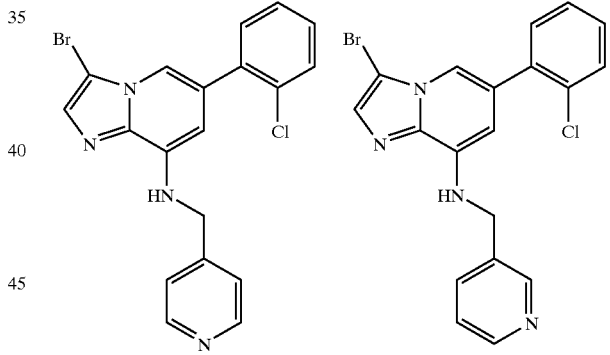
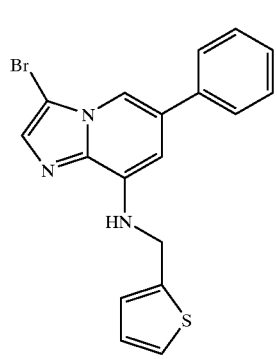
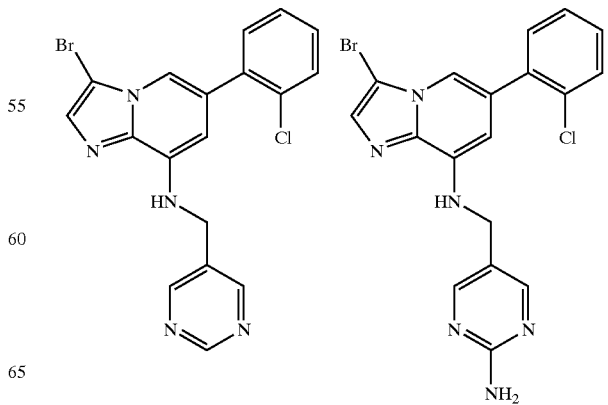

-continued
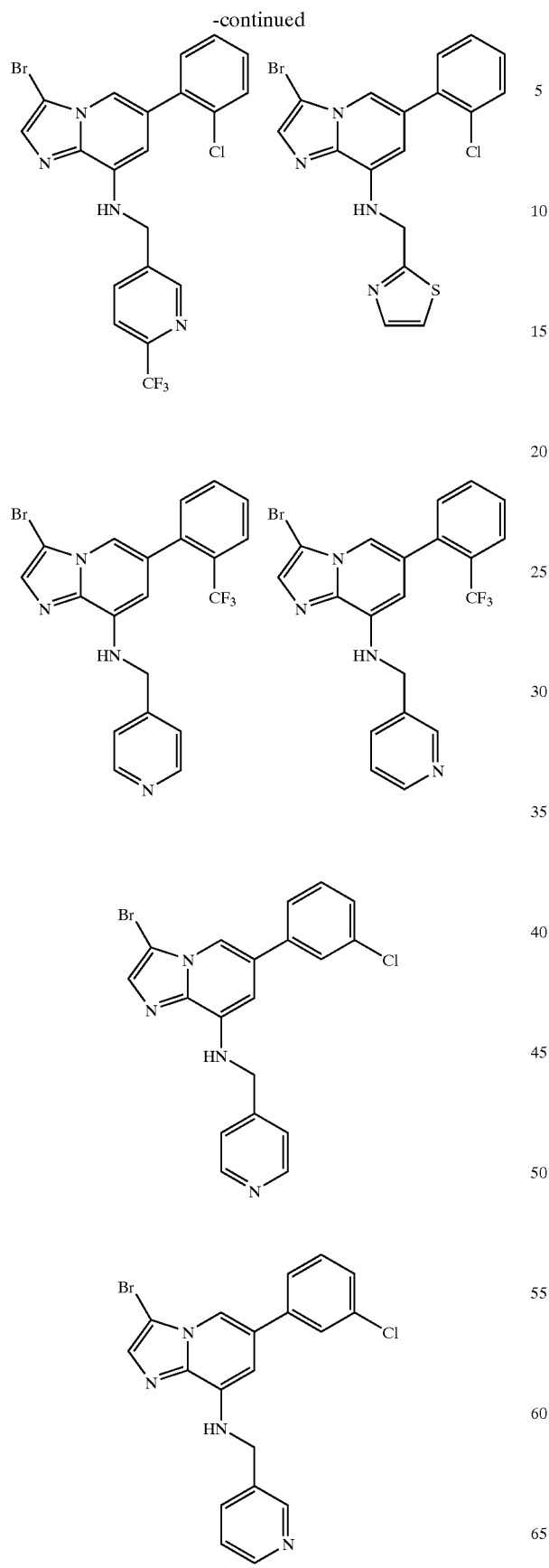
-continued
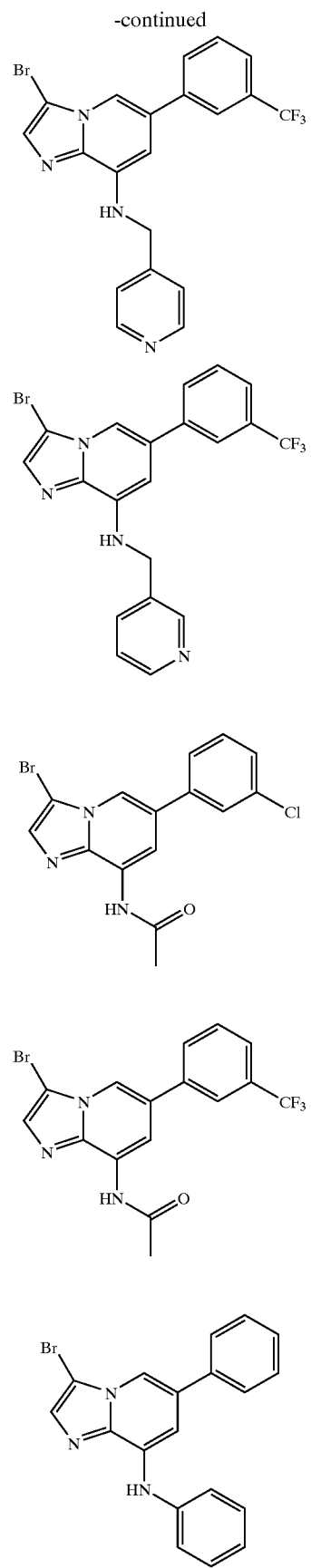

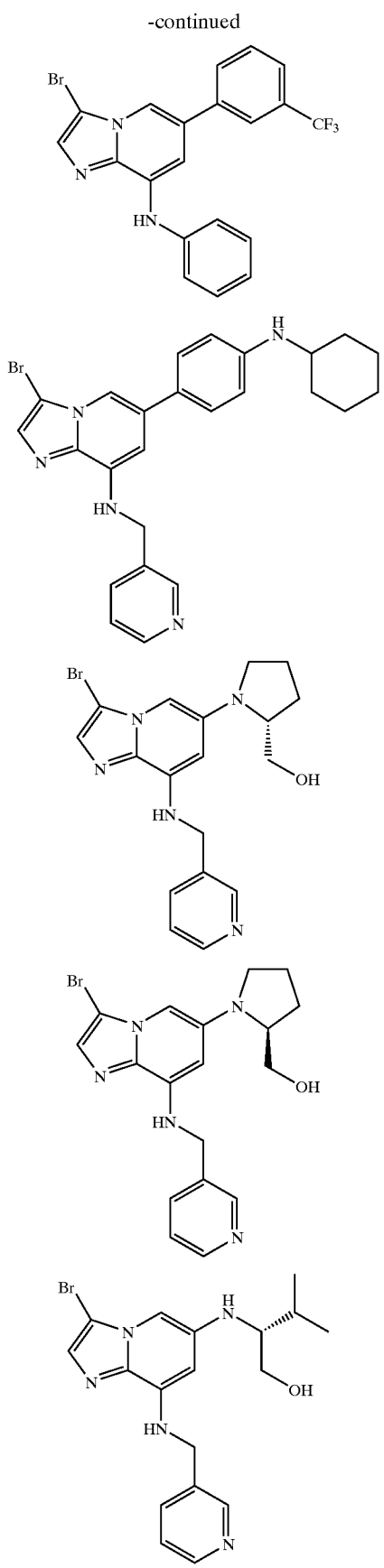
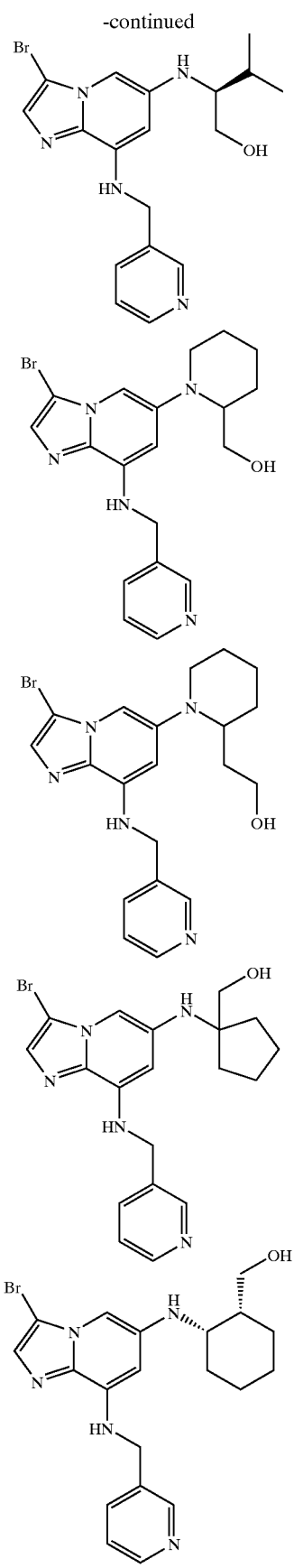

-continued
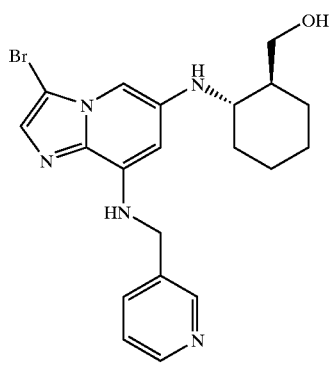
or
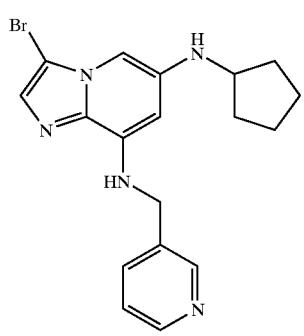
or a pharmaceutically acceptable salt or solvate thereof.
14. A compound of formula:
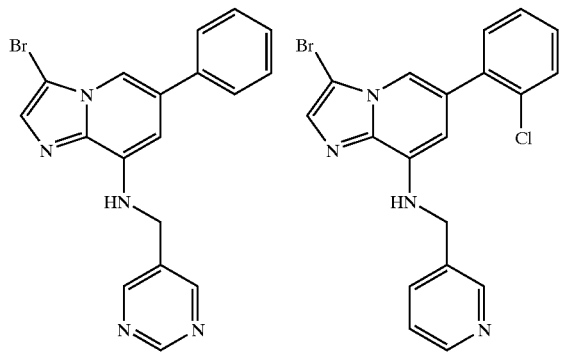
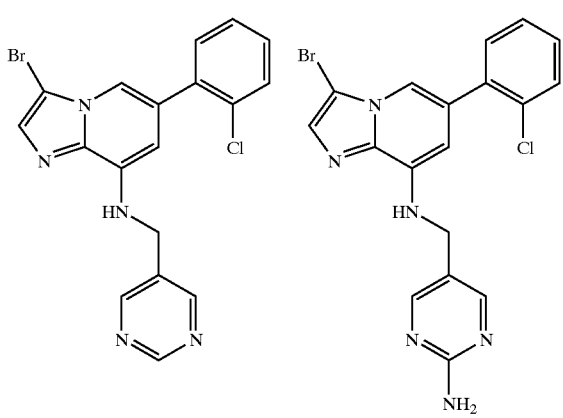
-continued
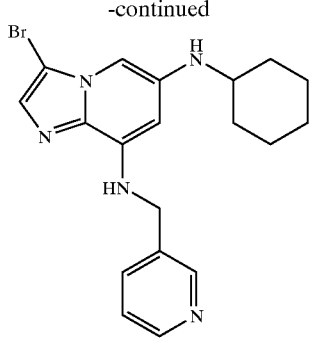
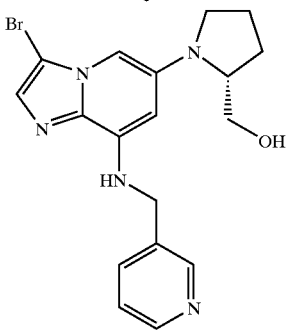
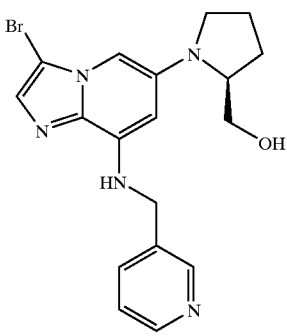
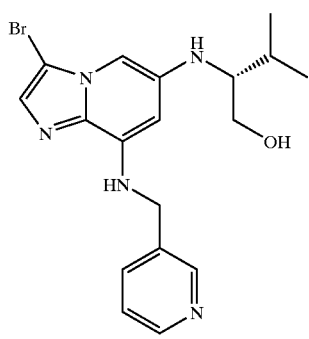
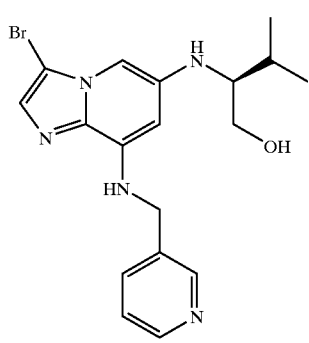

-continued
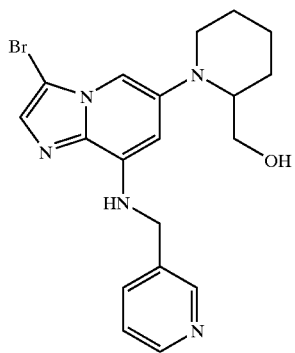
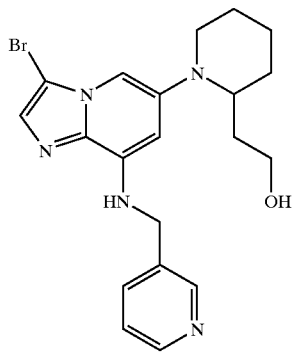
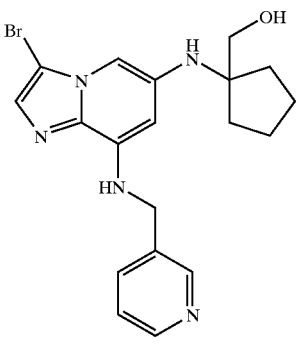
-continued
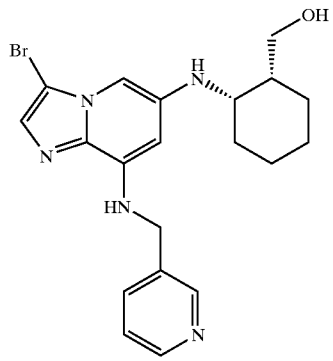
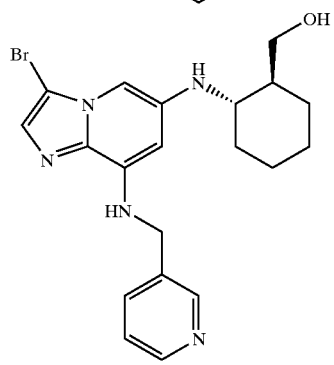
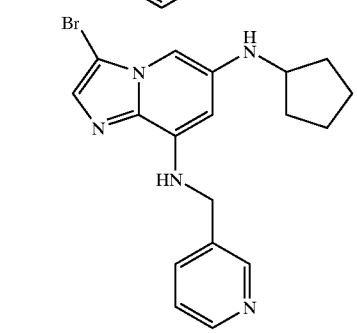
or
or a pharmaceutically acceptable salt or solvate thereof.
15. A pharmaceutical composition comprising a therapeutically effective amount of at least one compound of claim 1 in combination with at least one pharmaceutically acceptable carrier.
16. A compound of claim 1 in purified form.
* * * * *

UNITED STATES PATENT AND TRADEMARK OFFICE
CERTIFICATE OF CORRECTION

PATENT NO. : 6,992,080 B2  Page 1 of 1
APPLICATION NO. : 10/664338
DATED : January 31, 2006
INVENTOR(S) : Dwyer et al.

It is certified that error appears in the above-identified patent and that said Letters Patent is hereby corrected as shown below:

Col. 76, line 46:   Please correct "$NR^5R^7$" to -- $NR^6R^7$ --
Col. 76, line 54:   Please correct "$S(O_{2)R}^6$" to -- $S(O_2)R^6$ --
Col. 83, lines 15-25:   Please correct the following structure:

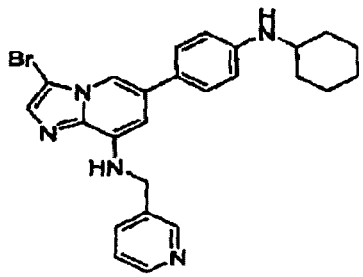

to the following structure:

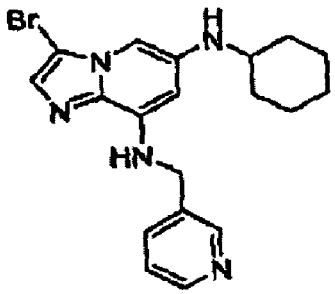

Signed and Sealed this

Third Day of October, 2006

JON W. DUDAS
*Director of the United States Patent and Trademark Office*